US005888781A

United States Patent [19]

Sierks et al.

[11] Patent Number: 5,888,781

[45] Date of Patent: Mar. 30, 1999

[54] METHOD FOR INCREASING THE HYDROLYTIC ACTIVITY OF STARCH HYRDOLASES

[75] Inventors: Michael Sierks, Cooksville; Sateesh Natarajan, Baltimore, both of Md.

[73] Assignee: University of Maryland Baltimore County, Baltimore, Md.

[21] Appl. No.: 815,851

[22] Filed: Mar. 12, 1997

[51] Int. Cl.[6] .............................. C12P 19/14; C12N 9/26; C13K 30/00

[52] U.S. Cl. ................................ 435/99; 435/201; 127/36

[58] Field of Search ..................... 435/195, 99, 200–211, 435/72, 95–105, 188; 127/34, 37, 36

[56] References Cited

U.S. PATENT DOCUMENTS 5,162,210 11/1992 Sierks et al. .............................. 435/96

OTHER PUBLICATIONS

Ceska, M. "Enzymatic reactions in the presence of non–ionic polymers," Experientia (1971) 27(7): 767–8, 1971.

Chen et al. "Lactose hydrolysis by beta–galactosidase in aqueous two–phase systems," J. Ferm. Bioeng. (1991) 71(3): 168–75, 1991.

Larsson et al. "Integration of bioconversion and downstream processing: Starch hydrolysis in an aqueous two–phase system," Biotechnol. Bioeng. (1989) 33: 758–66, 1989.

Delbourg et al. "Effect of PEG and other additives on cyclodextrin production by Bacillus macerans cyclomalto-dextrin–glycolsyl–transferase," Biotech. Lett. (1993) 15(2): 157–162, Feb. 1993.

Hayashida et al. "Enhancement of enzymatic production of cyclodextrans by adding polyethylene glycol or polypropylele glycol," J. Fermentation Bioeng. (1992) 7(3): 239–240, 1992.

Semichaevskii et al. "Hydrolysis of soluble starch by anylosubtitin G10x in media containing polyethylene glycol," Appl. Biochem. Microbiol. (1979) 45(2): 122–128, English translation, 1979.

Zaw et al, "Increasing the Catalytic Activity of Glucoamylase", *211th American Chemical Society National Meeting and Exposition Program*, pp. viii, 69 and Abstract, New Orleans, LA, (March 27–28, 1996).

*Primary Examiner*—Jon P. Weber
*Assistant Examiner*—Susan Hanley
*Attorney, Agent, or Firm*—Sughrue, Mion, Zinn, Macpeak & Seas, PLLC

[57] ABSTRACT

A method for increasing the catalytic rate of starch hydrolases comprising reacting a starch hydrolase with a substrate therefor in the presence of about 0.001 to 80% (w/v) of an ethylene glycol or polyethylene glycol.

10 Claims, 26 Drawing Sheets

METHOD FOR INCREASING THE HYDROLYTIC ACTIVITY OF STARCH HYRDOLASES

The development of present invention was supported by the University of Maryland, Baltimore County.

1. Field of the Invention

The present invention relates to a method for increasing the catalytic (turnover) rate of starch hydrolases.

2. Background of the Invention

I. Starch Hydrolases

Fungal glucoamylase (hereinafter "GA") (EC 3.2.1.3; 1,4-α-glucan glucohydrolase) is widely used in the food industry, most importantly in the production of glucose and fructose syrups from starch (Kennedy et al, *TIBTECH*, 6:184–189 (1988); Reilly, *In: Starch Conversion Technology*, van Beynum et al, eds., Marcel Dekker, Inc., New York, pp. 101–142 (1985)). The production of High Fructose Corn Syrup (HFCS) represents a multi-million dollar industry, and has progressed over the years from acid hydrolysis to a series of enzyme catalyzed reactions. Starch degradation by enzymes is preferred over acid hydrolysis in many industrial processes because of the specific hydrolysates and fewer by-products (Kennedy et al, supra). HFCS is produced from corn starch through three basic enzymatic reactions:

(i) degradation of the starch to maltodextrins, (ii) hydrolyzation of the maltodextrins to glucose, and (iii) isomerization of the glucose to fructose.

In a typical industrial process, following pretreatment of the starch, the first enzymatic reaction is catalyzed by α-amylase at 95° C. for 0.5–2 hrs. The second step, maltodextrin hydrolysis, is catalyzed by GA at 60° C. for 48–96 hrs. The final isomerization step is catalyzed by glucose isomerase at 90° C. for 30 min (Fullbrook, *In: Glucose Syrups: Science and Technology*, Dziedzic et al, eds., Elsevier Applied Science Publishers, LTD, Inc., New York, pp. 65–116 (1984); and Reilly, supra).

Because of the different pH optima and thermal stabilities of the three enzymes, each step in the process is run at a different temperature, and with a different buffer. The time required for the GA reaction represents approximately 95% of the entire process time. This is attributable primarily to the decreased thermal stability and slow turnover rate of GA (Kennedy et al, supra; and Chen et al, *Biochem. J.*, 301:275–281 (1994)). The efficiency of this process can be substantially improved by increasing the catalytic rate of GA.

GA catalyzes the release of D-glucose by hydrolysis of α-1,4- and α-1,6-glucosidic linkages at the non-reducing ends of starch and related oligosaccharides (Hiromi et al, *Mol. Cell. Biochem.*, 51:79–95 (1983)). Hydrolysis is thought to occur by a general acid catalyst donating a hydrogen to the glucosidic bond oxygen, and a catalytic base directing the nucleophilic attack of a water molecule (Frandsen et al, *Biochem.*, 33:13808–13816 (1994)). In GA from *Aspergillus awamori*, the general acid group has been identified as $Glu_{179}$ (Sierks et al, *Protein Eng.*, 3:193–198 (1990)), and the catalytic base has been identified as $Glu_{400}$ (Frandsen et al, supra). The active site of GA has generally been considered to have seven subsites where each subsite accommodates a glucosyl residue (Hiromi, *In: Proteins: Structure and Function*, Vol. 2, Funatsu et al, eds., Halsted Press, New York, pp. 1–46 (1972)). However, crystallographic analysis has shown little, if any, evidence of the distant subsites (Aleshin et al, *J. Mol. Biol.*, 28:575–591 (1994); and Aleshin et al, *J. Biol. Chem.*, 269:15631–15639 (1994)), and recent kinetic data have shown that several of the assumptions of the original subsite theory (Hiromi, (1972), supra) are not valid for GA (Natarajan et al, *Biochem.*, 35:15269–15279 (1996)). In the subsite theory as proposed by Hiromi, the hydrolytic step was assumed to be the rate-limiting step of the glucoamylase reaction. However, recently, the minimal kinetic mechanism for GA has been shown to be represented by the following reaction scheme:

$$E+S \rightarrow ES \rightarrow EP \leftarrow E+P$$

where the release of product was suggested to be the rate-limiting step (Natarajan et al, supra). The first step in this process represents the tightly bound enzyme-substrate (ES) complex, the second step represents bond hydrolysis forming the enzyme-product (EP) complex, and the last step is the proposed rate-limiting product-release mechanism. The kinetic parameters obtained for each of these steps indicate that the first two steps, i.e., substrate binding and bond hydrolysis, take place very quickly, at a rate of around 1500 $s^{-1}$ at 8° C., while the last step, i.e., the postulated product release step, occurs much more slowly, at a rate of only 0.3 $s^{-1}$ at 8° C. (Natarajan et al, supra).

The $Trp_{120}$ loop region of *A. awamori* GA has been shown to be critical for activity (Sierks et al, *Protein Eng.*, 2:621–625 (1989)), and plays a major role in the product release step of maltooligosaccharides (Sierks et al, *Biochem.*, 35:1865–1871 (1996)). A conformational change associated with the $Trp_{120}$ loop region may control the release of the reducing end product (Svensson et al, *Carbohydr. Res.*, 227:29–44 (1992); and Natarajan et al, supra). The rate of bond hydrolysis is over 4000-fold faster than product release (Natarajan et al, supra). Thus, the catalytic rate can be increased by several orders of magnitude by designing a way to facilitate product release, before the chemistry of bond hydrolysis becomes a limiting factor.

II. Reaction Solvents

Enzymatic catalysis should not be viewed as a static process between a rigid enzyme and substrate, but, rather, as a continuous dynamic process where internal and external motions of proteins and solvent molecules contribute to the sequence of catalytic steps. Various statistical thermodynamic models have been proposed to explain these fluctuations (Somogyi et al, *Bioch. Biophys. Acta*, 768:81–112 (1984)). Since critical protein dynamics must take place in enzyme active sites where many of the interactions are exposed to solvent, it was postulated in the present invention that varying solvent parameters would be a potential route to explore enzyme function. Many studies have been performed to investigate the effect of solution viscosity on the dynamics of protein motion and on catalysis (Ansari et al, *Science*, 256:1796–1798 (1992); Brooks et al, *J. Mol. Biol.*, 208:159–181 (1989); and Demchenko et al, *Biochim. Biophys. Acta.*, 998:196–203 (1989)). The overall conclusion from these studies is that complex interactions occur between solvent and protein, as well as between molecules within the protein, and that current understanding of protein structure is not capable of fully explaining these interactions. Varying the hydration of enzymes has also been shown to have a profound effect on activity (Rupley et al, *Trends Biochem. Sci.*, 8:18–22 (1983); and Affleck et al, *Proc. Natl. Acad. Sci., USA*, 89:1100–1104 (1992)). Solvent viscosity and hydrophobicity can therefore, have significant effects on enzyme activity.

Kramers' theory (Kramers, *Physica*, 7:284–304 (1940)), which assumes that passing over the activation energy barrier is a function of diffusional motion in a random field, suggests that the catalytic rate should be inversely proportional to the solvent viscosity. This theory has been applied to some enzyme processes (Demchenko et al, supra; and Ansari et al, supra). However, it is not clear whether the model is generally applicable. The model describes the effects of temperature and solution characteristics on a rate-limiting enzymatic conformational isomerization step. This model however, may not adequately describe non-unimolecular processes, such as ligand binding and product release. A different model has been proposed to explain the dependence of ligand association and dissociation on solvent viscosity (Somogyi et al, *J. Theor. Biol.*, 48:393–401 (1975); Somogyi et al, *J. Theor. Biol.*, 74:209–216 (1978); and Welch et al, *J. Theor. Biol.*, 100:211–238 (1993)). For a ligand, either substrate or product, to dissociate from the active site of an enzyme, the ligand must have sufficient kinetic energy to allow it to escape a given "recognition volume". As long as the ligand is within the "recognition volume" it may reassociate with the enzyme. However, once it leaves this "recognition volume", it will not reassociate. The viscosity of the media will influence the rate at which product can dissociate from the active site by increasing the energy required to escape the "recognition volume". The enzymatic turnover rate will have a second order dependence on viscosity if substrate association or product dissociation is the rate-limiting step for the reaction.

The nature of the solvent may have very profound effects on enzyme catalysis, including varying local hydration levels, varying the ordered solvent layer surrounding the protein, and influencing the dynamic interactions of local protein molecules in the active site as well as global interactions. The solvent may also have similarly effects on the substrate molecule, although once the substrate is bound in the enzyme active site, the enzyme/substrate complex is subjected to its own microenvironment. Clearly though, solvent viscosity effects can play a significant role in protein dynamics.

In the present invention, additional evidence has been developed that product release step represents the rate-limiting step in the GA mechanism. Further, potential methods to influence this step were investigated in the present invention using various viscogenic cosolvents.

III. Polyethylene Glycol

Polyethylene glycol (hereinafter "PEG") has been used in the food industry to increase the viscosity of solutions, as a thickener, e.g., in jelly, ice cream, sauces, etc.

However, heretofore, when PEG has included in enzymatic reaction solutions, i.e., solutions containing enzymes, their substrates, and appropriate buffers and salts, the catalytic rate of the enzymes has decreased (Ansari et al, supra; Brooks et al, supra; and Demchenko et al, supra).

On the other hand, it has been discovered in the present invention that when PEG is included in a starch hydrolase enzymatic reaction solution, the catalytic rate of the starch hydrolase is increased.

SUMMARY OF THE INVENTION

An object of the present invention is to provide a method for increasing the catalytic rate of a starch hydrolase.

Another object of the present invention is to provide a method which allows for a reduced reaction time in a starch hydrolase reaction.

Still another object of the present invention is to provide a method which allows for a reduced starch hydrolase reactor size.

Yet another object of the present invention is to provide a method which allows for a reduction in the cost of carrying out a starch hydrolase reaction.

These and other objects of the present invention, which will be apparent from the detailed description of the invention provided hereinafter, have been met in one embodiment, by a method for increasing the catalytic rate of a starch hydrolase comprising reacting a starch hydrolase with a substrate therefor in the presence of about 0.001 to 80% (w/v) of an ethylene glycol.

DETAILED DESCRIPTION OF THE INVENTION

Figure 1A:
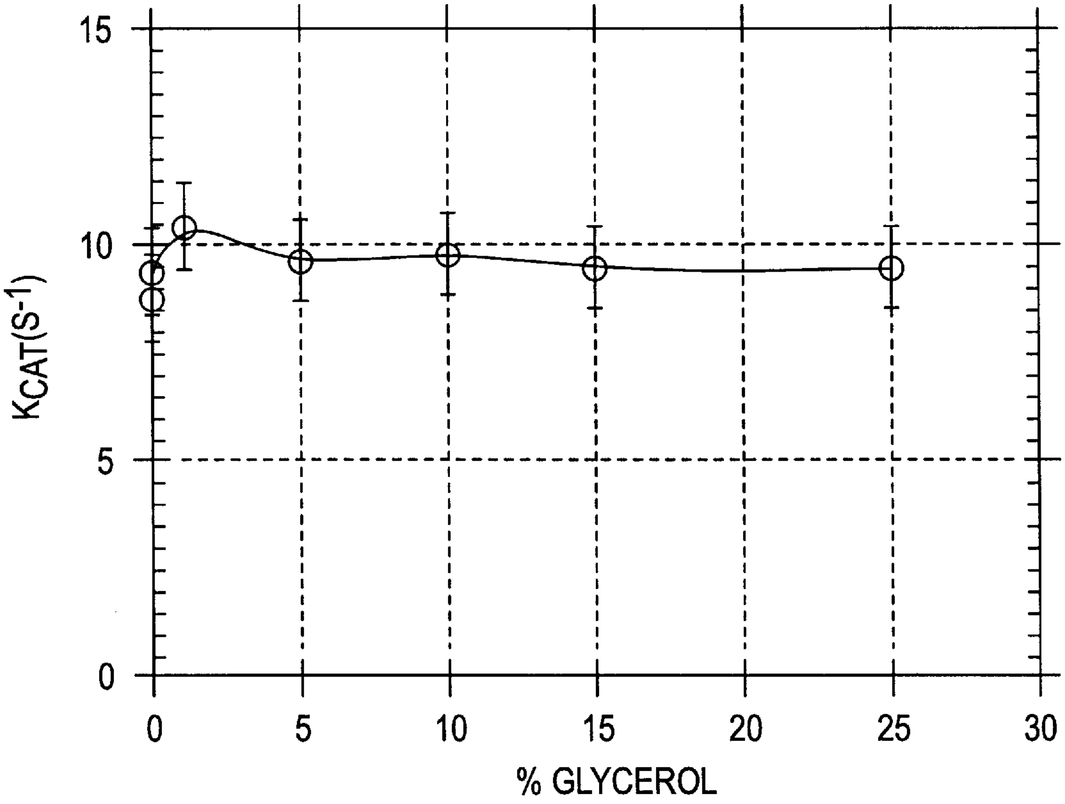
FIGS. 1A–1G show plots of $k_{cat}(s^{-1})$ vs cosolvent concentration (% (w/v)) for maltose hydrolysis by GA at 45° C., 0.05M sodium acetate buffer (pH 4.5) in the presence of: glycerol (FIG. 1A); PVP (FIG. 1B); EG (FIG. 1C); TEG (FIG. 1D); PEG200 (FIG. 1E); MEG (and also data at 60° C. (□)) (FIG. 1F); and PEG8000 (and also data at 60° C. (□)) (FIG. 1G).

As discussed above, in one embodiment, the above-described objects of the present invention have been met by a method for increasing the catalytic rate of a starch hydrolase comprising reacting a starch hydrolase with a substrate therefor in the presence of about 0.001 to 80% (w/v) of an ethylene glycol or polyethylene glycol.

The particular starch hydrolase employed is not critical to the present invention. Examples of such starch hydrolases include glucoamylase, α-amylase, β-amylase, amylo-1,6-α-glucosidase, isomaltase, maltotriase, maltase, α-glucosidase, cyclodextrin, pullulanase, branching enzyme and glucanotransferase (Svensson et al, *FEBS Lett.*, 230:72–76 (1988); MacGregor et al, *Biochem. J.*, 259:145–152 (1989); and Jespersen et al, *Biochem. J.*, 280:51–55 (1991)).

The substrate employed in the reaction solution is not critical to the present invention, and will vary depending upon the substrate specificity of the starch hydrolase employed. Substrates for the above-listed enzymes are well-known in the art. For example, isomaltose is a substrate for isomaltase; starch and maltodextrin are substrates for α-amylase; and pullulan is a substrate for pullulanase.

Buffers and salts used to carry out reactions with starch hydrolases are well-known in the art (Fullbrook, supra; and Reilly, supra; which are incorporated by reference herein).

The particular ethylene glycol (EG) or polyethylene glycol (PEG) employed is not critical to the present invention. The EG and PEG may be conventional EG or PEG, as well as derivatives thereof. Examples of such PEG include, tetraethylene glycol (TEG), polyethylene glycol 200 (PEG200), polyethylene glycol 8000 (PEG8000), and methoxypolyethylene glycol (MEG).

The degree of polymerization of the PEG is also not critical to the present invention. For example, degree of polymerization can be from 2 to 10,000, preferably about 200 to 8000.

However, the maximum increase in activity, up to 65%, was found to be obtained with cosolvents having a degree of polymerization of 200 or higher. Further, the longer the polymer, the lower the concentration needed to obtain the maximum increase in activity.

Use of PEG1000 and PEG8000 are preferred as such are non-toxic, i.e., there is no need to remove the PEG from the reaction product, e.g., glucose syrup.

The amount of EG/PEG employed in the method of the present invention is preferably in the range of about of about 0.01 to 20% (w/v), more preferably about 0.01 to 10% (w/v), most preferably about 0.01 to 1.0% (w/v). The longer molecular weight PEG gives the best results when used at lower concentrations.

The reaction temperature is not critical to the present invention. Generally, the reaction temperature will range from 45° to 75° C., preferably from 60° to 65° C.

The standard reaction to hydrolyze glucose from maltodextrin takes up to 2–3 days to reach completion (Reilly, supra). However, using the method of the present invention it is possible to reduce the reaction time by about one-half, i.e., to reach completion in 1–2 days.

Use of EG/PEG in the present invention can give rise to an increase of catalytic rate of up to about 80%. As a result, the reaction time can be decreased, and well as the size of the reactor. Further, the cost of carrying out the reaction can be reduced.

The following examples are provided for illustrative purposes only, and are in no way intended to limit the scope of the present invention.

EXAMPLE 1

Effect of Cosolvents on Catalytic Rate

Seven different cosolvents were utilized to study (i) the effect of the individual cosolvents on the reaction mechanism of GA from *A. awamori*; and (ii) the effect of solution viscosity on the reaction mechanism of GA from *A. awamori.*

GA was produced in *Saccharomyces cerevisiae* and obtained, as described by Natarajan et al, *Biochem.*, 35:3050–3058 (1996).

Four of the cosolvents used represent a series of different degrees of polymerization of ethylene glycol, i.e., EG, TEG, PEG200 and PEG8000. The fifth cosolvent used is a methylated derivative of polyethylene glycol, i.e., MEG, having an average degree of polymerization of 350. The sixth cosolvent used has a repeating ethyl backbone, i.e., polyvinylpyrrolidone (PVP) having an average molecular weight of 10,000. The seventh cosolvent used is a monomeric cosolvent structurally similar to EG, i.e., glycerol. All of these cosolvents were obtained from Sigma (St. Louis, Mo.).

A. GA Activity Assays

Kinetic assays were performed either at 45° C. or at 60° C., in 0.05M sodium acetate buffer (pH 4.5), using a substrate, i.e., maltose, concentration of 20 mM. The substrate concentration was sufficiently above the $K_m$ value so that the measured rate was directly proportional to $k_{cat}$. The enzyme concentrations used in the reaction mixtures were 35 μg/ml and 3.5 μg/ml for the 45° C. and 60° C. experiments, respectively.

Protein concentrations were determined using $OD_{280}$ nm, and an extinction coefficient of $e_m=1.37\times10^5 M^{-1}\ cm^{-1}$ (Clarke et al, *Carlsberg Res. Commun.*, 49:111–122 (1984)).

The cosolvent solutions were prepared from a concentrated cosolvent mixture by dilution to the final concentrations ranging from 0–90% (w/v), into the appropriate reaction buffer solution. The buffer solutions were titrated for pH prior to addition of cosolvent. All of the solutions were equilibrated at 45° C. (or 60° C.) in a water bath, and the reaction was started by the addition of a 25 μl aliquot of enzyme. Reaction aliquots were removed at various times, and the reaction was stopped by the addition of 2.5M Trizma base (pH 7.0). All of the reactions were performed in duplicate. The rates were determined by measuring the concentration of the released glucose by the glucose oxidase method, using the Glucose Oxidase Kit (Sigma), as modified for microtiter plate assays, at $OD_{450}$ nm (Fox et al, *Anal. Biochem.*, 195:93–96 (1991); and Palcic et al, *Carbohydr. Res.*, 250:87–92 (1993)), and using an EL 340 biokinetics reader (BIOTEK Instruments; Winooski, Vt.).

Glucose standards at each of the various cosolvent concentrations were run parallel to each reaction so that any effect of the cosolvents on the glucose assay could be subtracted out.

The effect of the cosolvents on the catalytic rate of GA are shown in FIGS. 1A–1G.

Figure 1B:
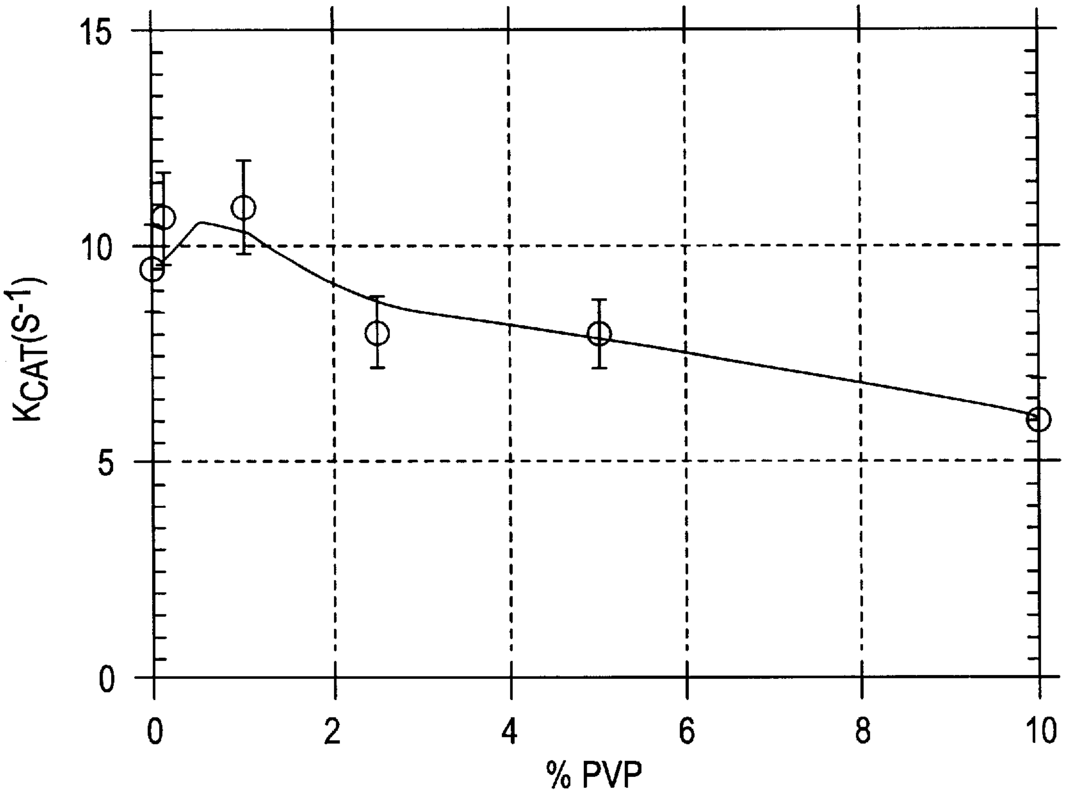

As shown in FIGS. 1A–1B, with two of the cosolvents, i.e., glycerol (FIG. 1A) and PVP (FIG. 1B), only a minor increase in $k_{cat}$ was observed at around 1.0% (w/v) cosolvent concentration, although this increase was not statistically significant.

On the other hand, as shown in FIGS. 1C–1G, all of the PEG based cosolvents, i.e., EG (FIG. 1C), TEG (FIG. 1D), PEG200 (FIG. 1E), PEG8000 (FIG. 1F) and MEG (FIG. 1G), gave substantial increases in the $k_{cat}$ values at varying concentrations, with PEG8000, PEG200, and MEG exhibiting the largest increases.

Figure 1C:
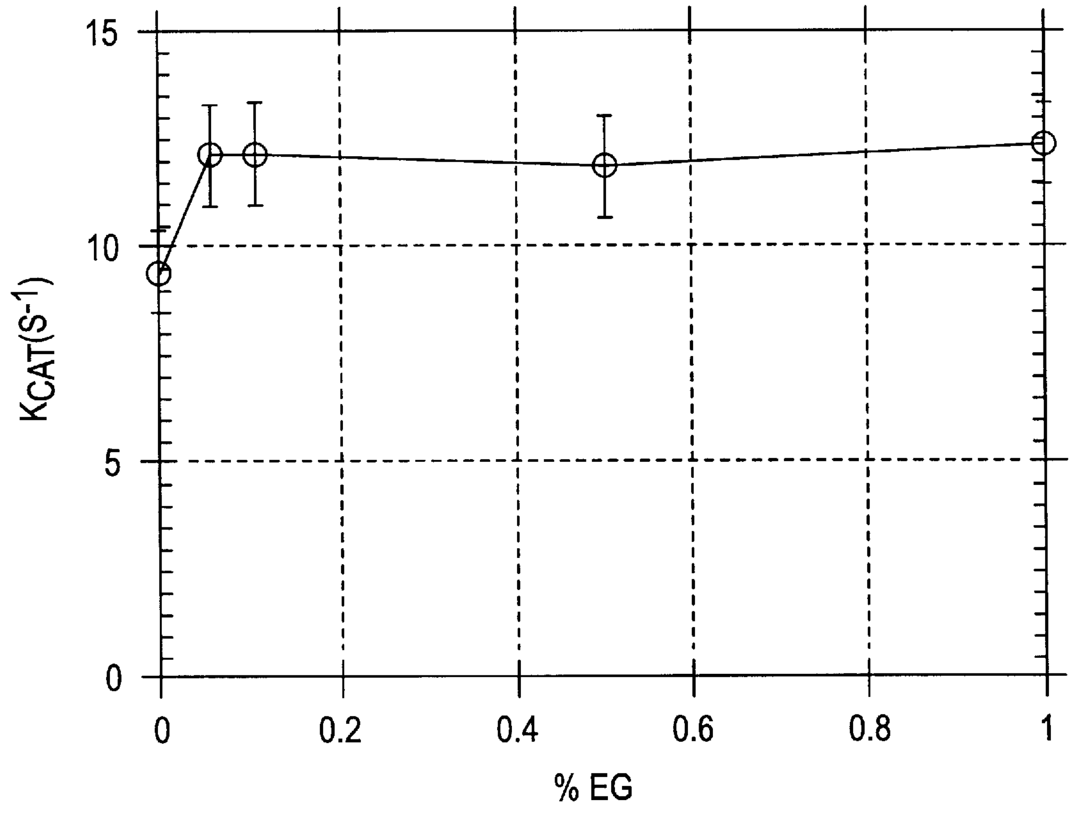
Figure 1D:
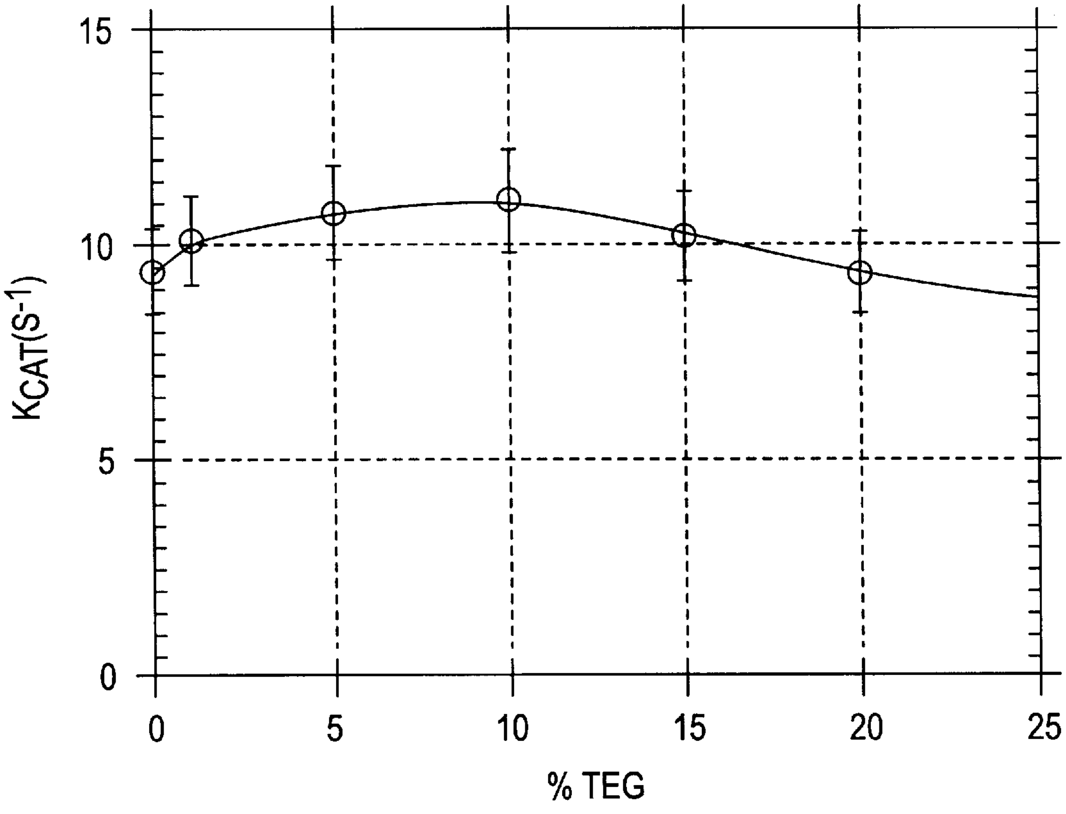
Figure 1E:
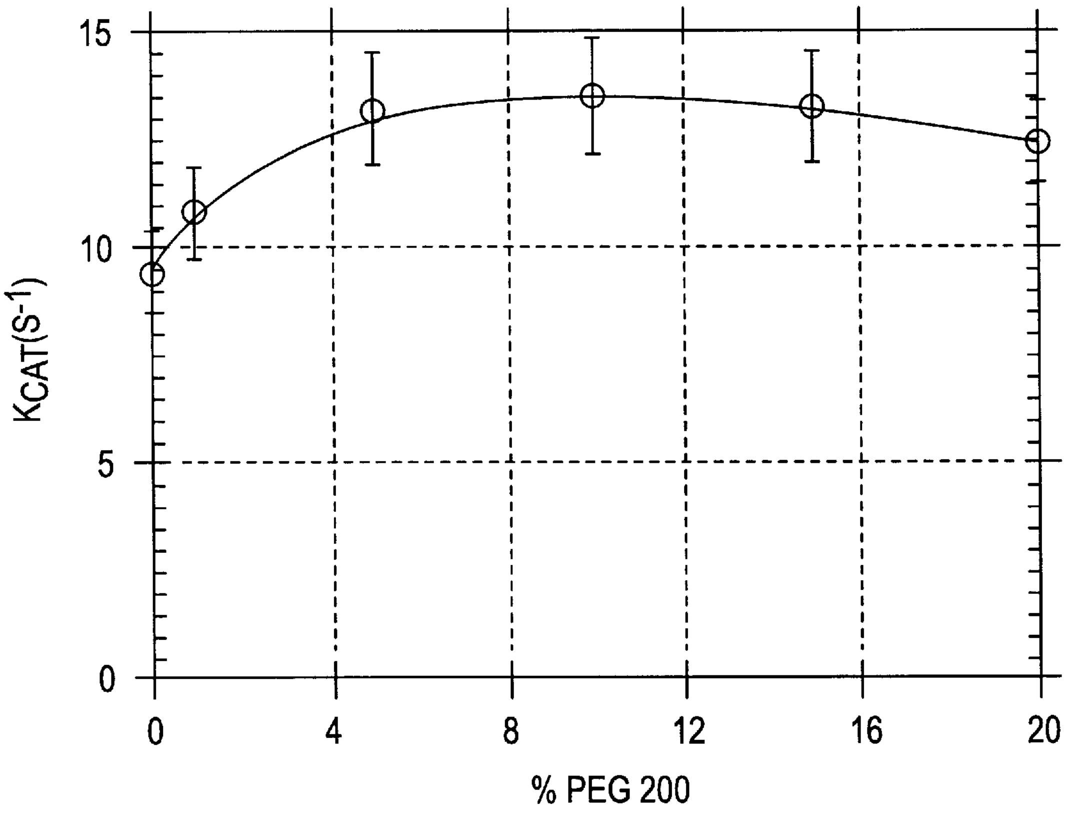
Figure 1F:
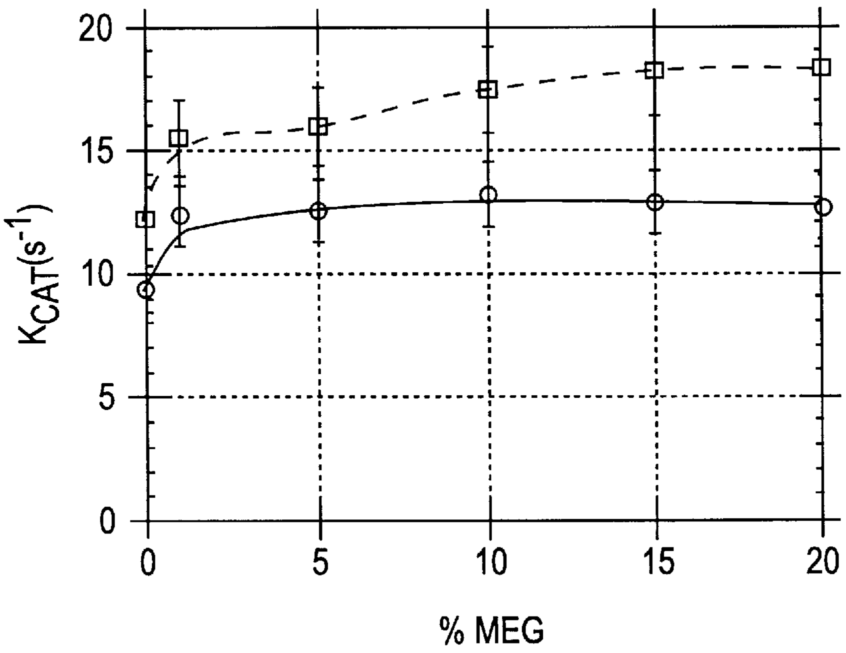
Figure 1G:
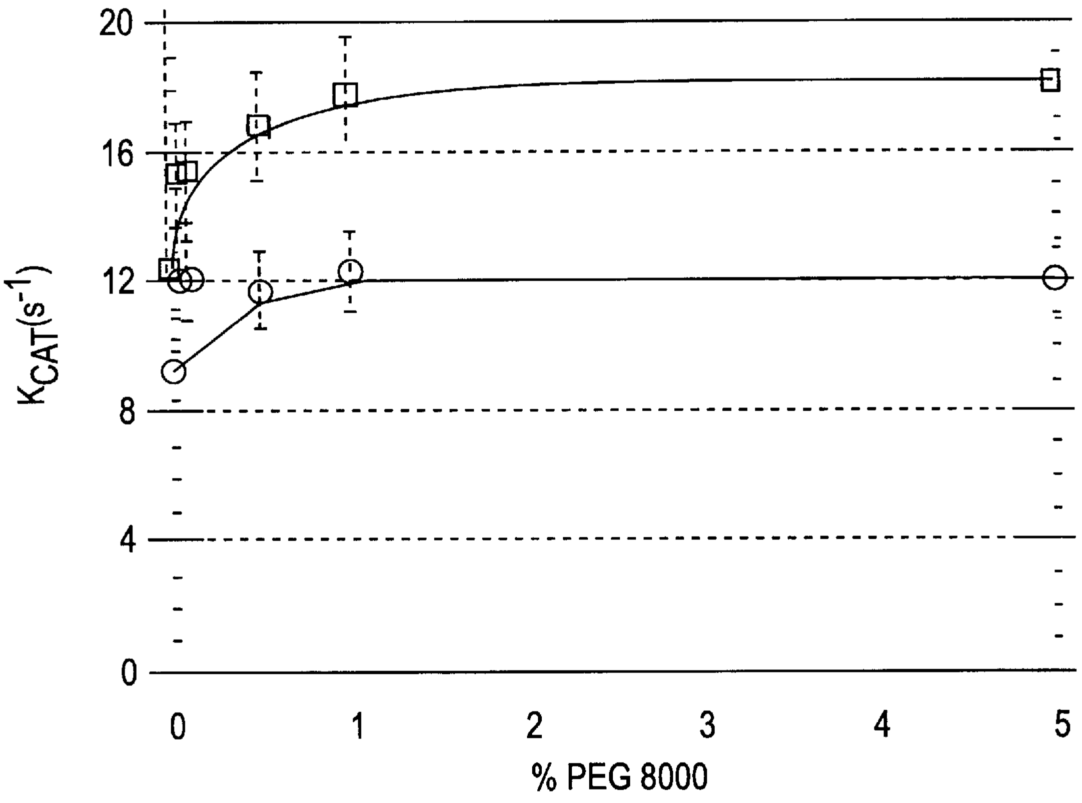

As shown in FIGS. 1G and 1C, respectively, a substantial increase in the $k_{cat}$ value is first noticed at very low concentrations with the longest polymer (0.01% (w/v) PEG8000), and at much higher concentrations with the monomer (50% (w/v) EG). Since neither the monomeric cosolvent glycerol, nor the polymeric cosolvent PVP, gave statistically significant increases in $k_{cat}$, the observed increase in turnover rate with the EG-based cosolvents cannot be attributed to any nonspecific effects of the added cosolvent. The increase in rate appears to be due to a specific interaction of the EG-based cosolvents with the enzyme that somehow facilitates the kinetic mechanism.

Cosolvents may alter the $pK_a$ values of the catalytic groups of enzymes due to local changes in the enzyme environment (Bernard et al, *J. Am. Chem. Soc.*, 74:6099–6101 (1952)). To test if the observed increase in $k_{cat}$ value might be caused by changes in the pH dependence of GA, the $k_{cat}$ values for maltose hydrolysis in 10% (w/v) PEG200 at a pH ranging from 2.8–7.4, were measured. The results demonstrated only a very slight downward shift in the pH optimum. This indicates that the cosolvent does not significantly alter the enzyme $pK_a$ values.

The maximum percent increase in the $k_{cat}$ value, and the concentration where those values occur for each of the seven cosolvents, are shown in the Table below.

TABLE

Maximum Percent Increase in $K_{cat}$ for Maltose Hydrolysis by GA at 45° C. Over Control Value Without Cosolvent and Corresponding Cosolvent Concentrations

| Buffer | Concentration | $k_{cat}(s^{-1})$ | % Increase |
|---|---|---|---|
| PVP | 1.0% | 10.9 | 16 |
| Glycerol | 1.0% | 10.4 | 11 |
| PEG8000 | 1.0% | 13.6 | 45 |
| PEG8000 @ 60° C. | 1.0% | 25.2 | 68 |
| PEG200 | 10% | 13.5 | 43 |
| MEG | 10% | 13.2 | 40 |
| MEG @ 60° C. | 10% | 24.5 | 63 |
| TEG | 10% | 11.1 | 18 |
| EG | 50% | 12.4 | 32 |

As shown in the Table above, the effects of the different EG cosolvents on GA activity vary considerably. EG has its largest effect on $k_{cat}$ at concentrations around 50% (w/v); TEG, PEG200 and MEG at concentrations around 10% (w/v); and PEG8000 at concentrations around 1.0% (w/v). A straightforward assessment of the length dependence of the PEG cosolvents on the increase in $k_{cat}$ is somewhat complicated, since the longer polymers even at low concentrations, increase the solution viscosity. An increase in solution viscosity may decrease $k_{cat}$ since the rate-limiting step in the enzyme mechanism may be affected by viscosity. There are two competing effects that take place when the EG-based cosolvents are added to the reaction media; first, the presence of EG-based cosolvents specifically interact with the enzyme to facilitate the product release step, and second, presence of the cosolvents will increase the solution viscosity which may inhibit the ability of the enzyme to undergo conformational changes, thereby slowing down the product release step, or it may increase the required kinetic energy of the product to escape the enzyme active site. The expected result of these competing effects is that $k_{cat}$ would increase at low cosolvent concentration and decrease at higher concentrations as the viscosity effect starts to dominate.

The maximum increase in activity (Table above) does not seem to be dependent on the degree of polymerization past a certain point, as PEG200, MEG and PEG8000 increase $k_{cat}$ to similar extents, while TEG and EG produce significantly lower increases. With TEG, PEG200 and PEG8000 the increase in $k_{cat}$ reaches a plateau region with little or no decrease over a very broad concentration range, while with EG and MEG there is some decrease in $k_{cat}$ at higher cosolvent concentrations. The methoxy substitution in MEG apparently interferes somewhat with the specific interaction between the EG-based cosolvents and GA.

The interactions between cosolvents, such as PEG and various proteins are not entirely known, although the cosolvents have been known to increase or decrease protein stability and to decrease the rates of various steps in catalytic reactions. There are several postulated explanations for the cosolvent effects on proteins (Gekko et al, *Biochem.*, 20:4667–4676 (1981)). Since polymeric cosolvents, such as PEG, are hydrophobic, they may effect the salvation of the enzyme. The polymer may reduce the volume available to a protein, and thus increases the rigidity of the protein. This is not a likely explanation for the observed increase in GA activity, since no increase was seen with glycerol or PVP. A second possible explanation would be that steric effects caused by the long polymers interfere with the protein. This is a plausible explanation for the PEG cosolvents, as there is a definite polymer length dependence. However, addition of PVP does not increase $k_{cat}$, so stearic effects do not adequately explain the increase in GA activity. Another potential explanation is that since the protein is preferentially hydrated over the cosolvent, there may be some solvation effects which enhance the turnover rate. Once again since no increase was observed with either glycerol or PVP, solvation effects do not adequately explain the increase in $k_{cat}$. A possible explanation may be that the hydrophobic character of PEG interacts with a hydrophobic region on the enzyme, which facilitates the product release step. The repeating EG units of the polymers may contribute to the specificity of this interaction. Since the $Trp_{120}$ loop region of GA is involved in the rate-limiting product release step, the hydrophobic $Trp_{120}$ residue may be involved in this process. Further, since PEG8000 increases $k_{cat}$ at much lower concentrations than PEG200, MEG, or TEG, polymer length has some role in this interaction. Perhaps the longer polymers are joining two different sites on the enzyme or even different enzyme molecules, the result being a conformation that facilitates product release. Since the presence of EG also increases the turnover rate of GA, although at much higher concentrations than the other EG-based cosolvents, the increase in GA activity apparently can be attributed to some specific cosolvent effects, as well as a polymer length dependence.

B. Viscosity Determination

All buffers of various cosolvent concentrations were filtered before use. Viscosity and density measurements were performed using an Ostwald Capillary Viscometer at 45° C. The densities of the various buffer solutions were obtained by replicate weighing of one milliliter volumes of buffer. The relationships between the $K_{cat}$, as determined is described in Example 1 above, and the viscosities of the cosolvent are shown in FIGS. 2A–2G.

Figure 2A:
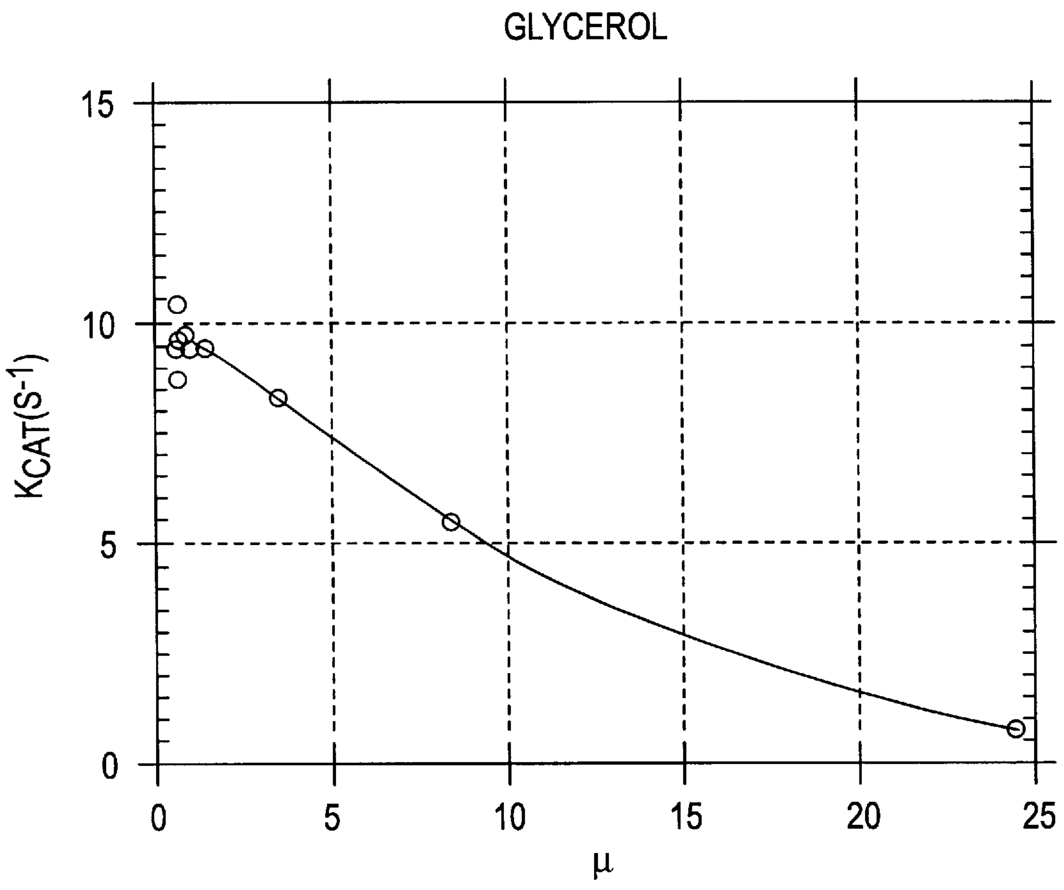
FIGS. 2A–2G show plots of $k_{cat}(s^{-1})$ vs solution viscosity ($\mu$) for maltose hydrolysis by GA at 45° C., 0.05M sodium acetate buffer (pH 4.5) in the presence of: glycerol (FIG. 2A); PVP (FIG. 2B); EG (FIG. 2C); TEG (FIG. 2D); PEG200 (FIG. 2E); MEG (FIG. 2F); and PEG8000 (FIG. 2G).
Figure 2B:
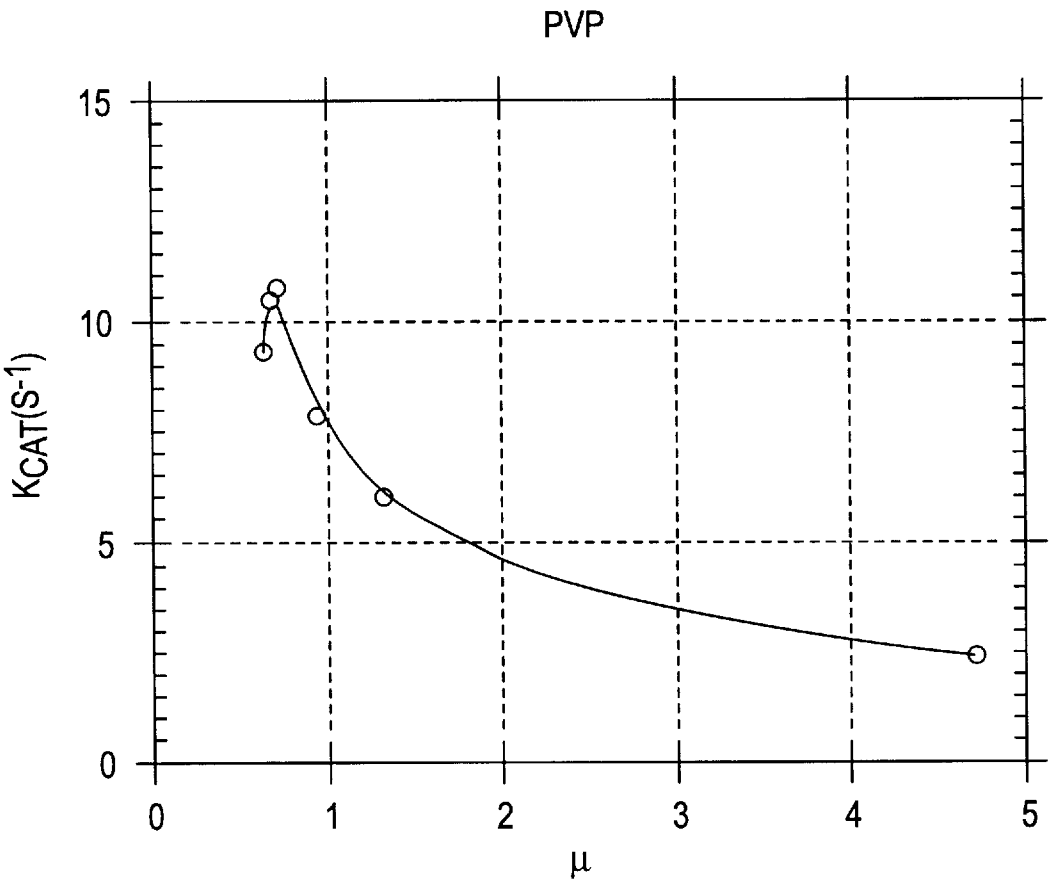
Figure 2C:
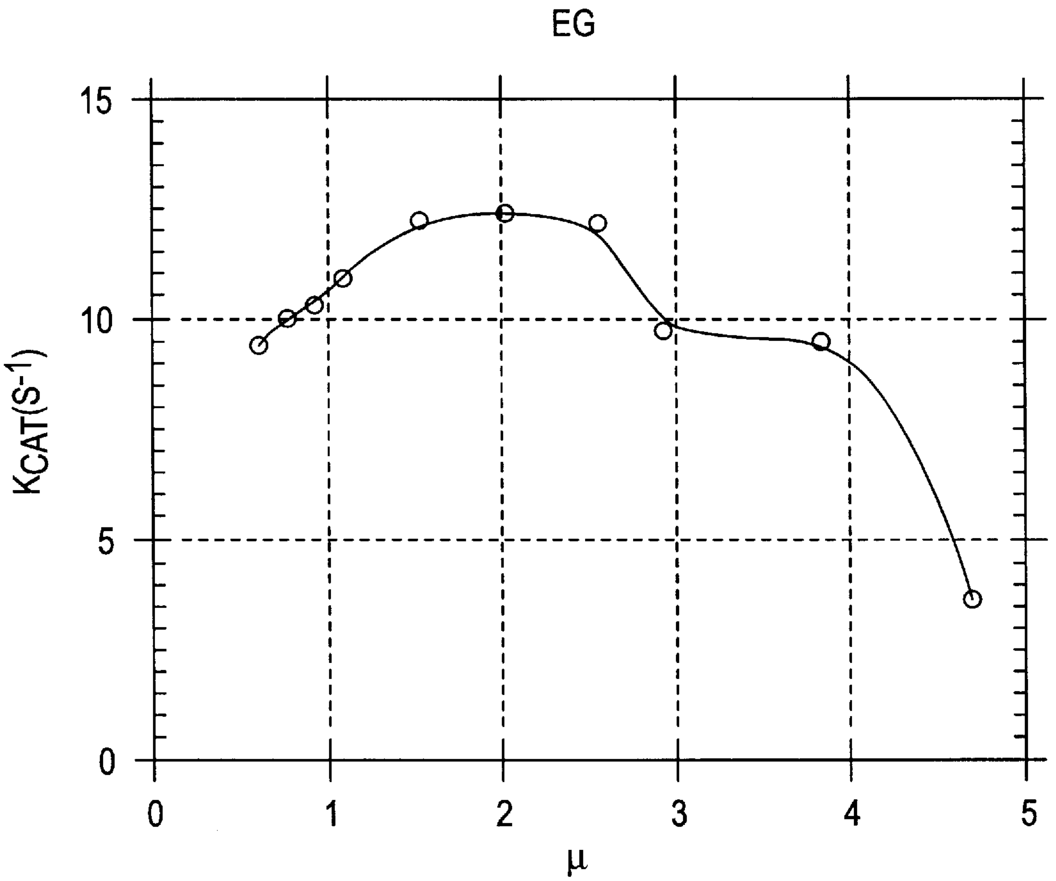
Figure 2D:
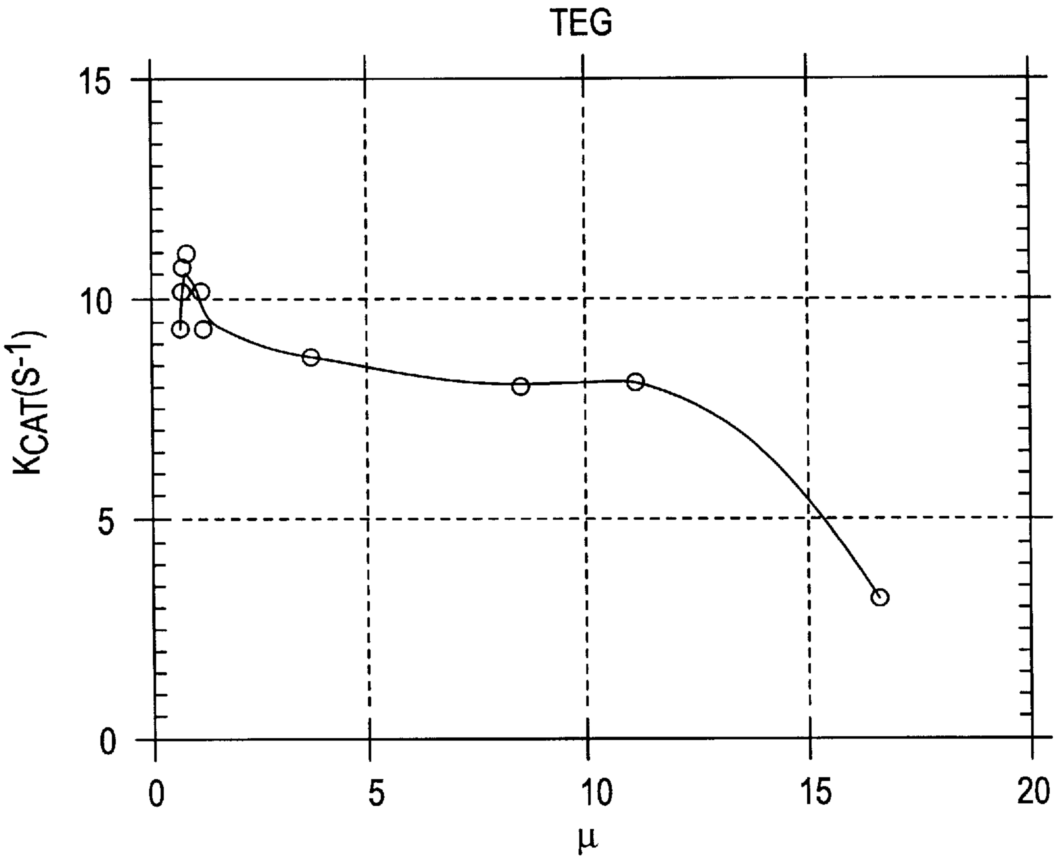
Figure 2E:
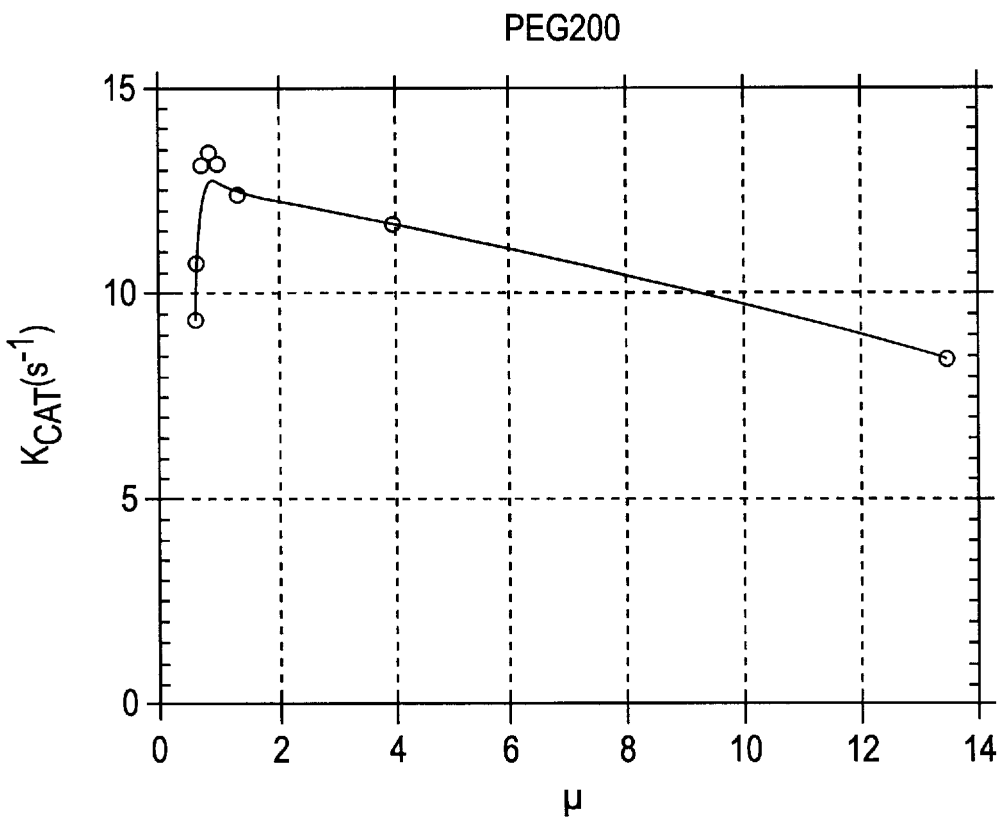
Figure 2F:
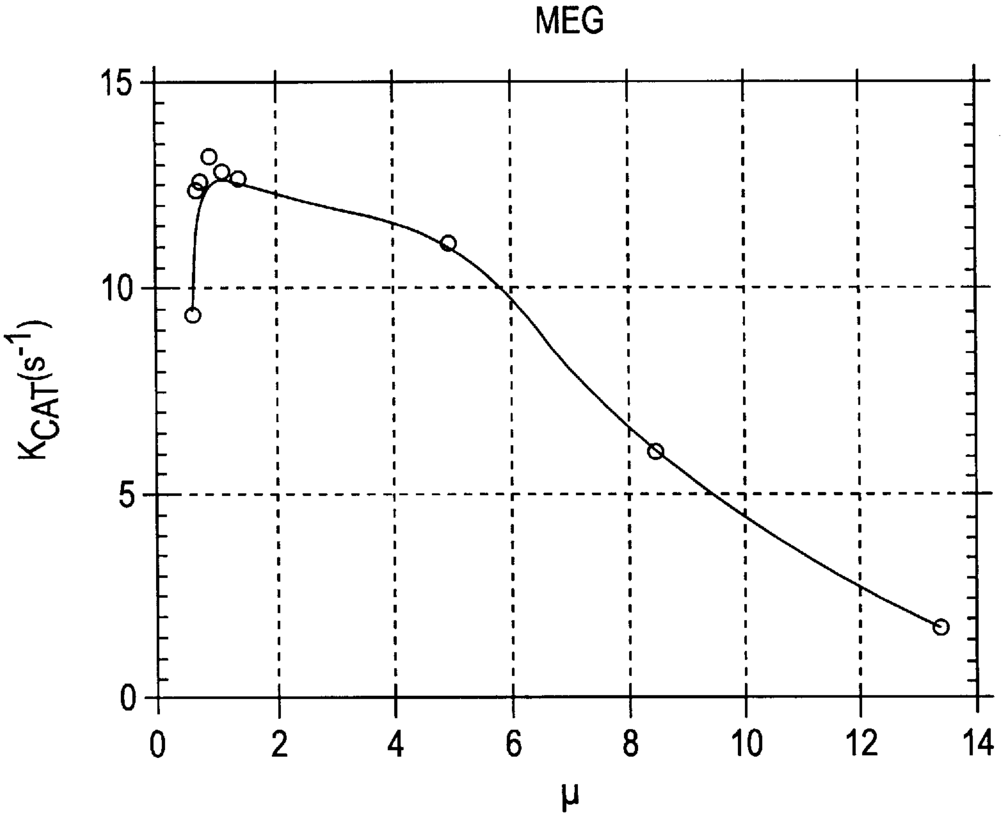
Figure 2G:
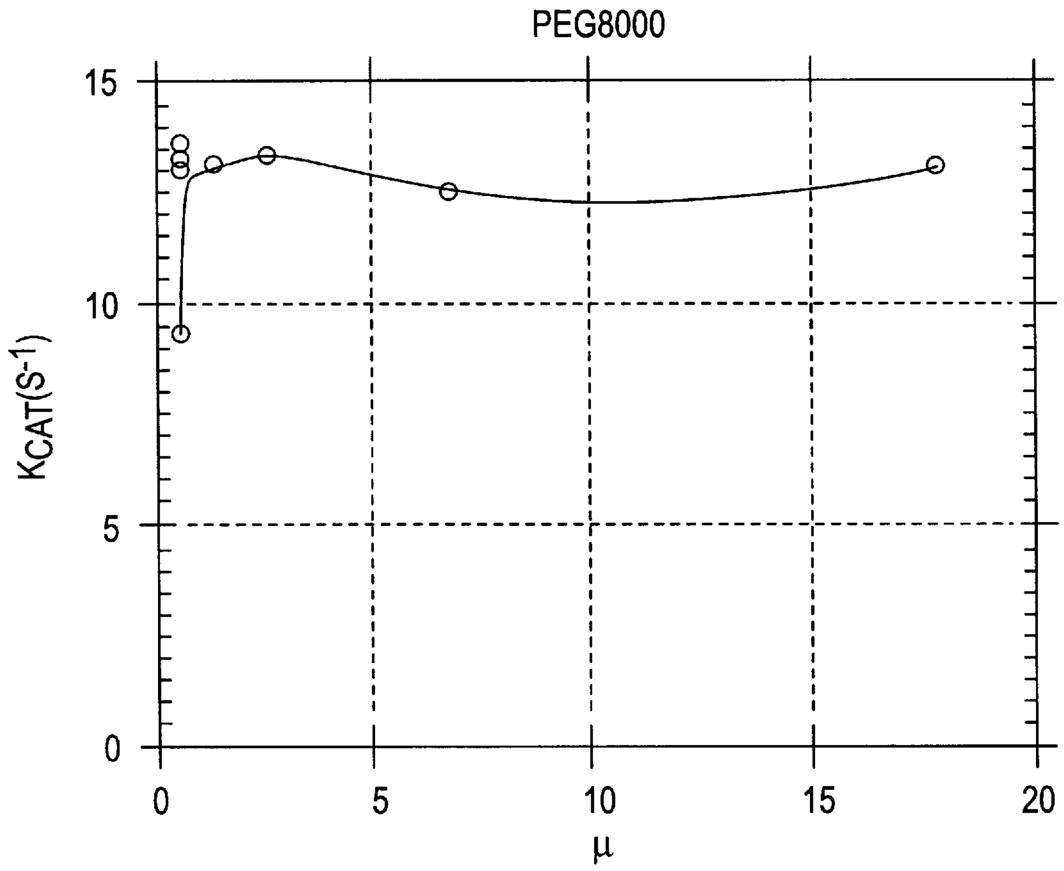
Figure 3A:
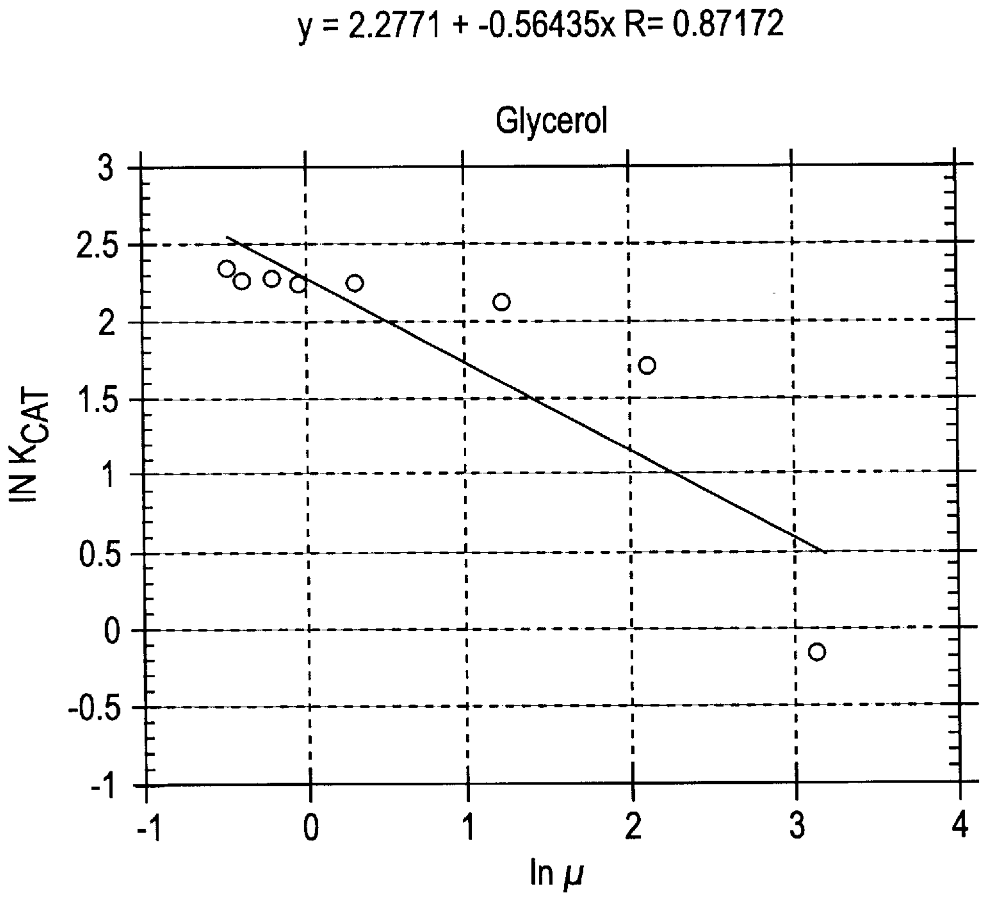
FIGS. 3A–3E show plots of $\ln(k_{cat})$ vs $\ln(\mu)$ for maltose hydrolysis by GA at 45° C., 0.05M sodium acetate buffer (pH 4.5) in the presence of: glycerol (FIG. 3A); PVP (FIG. 3B); EG (FIG. 3C); TEG (FIG. 3D); and MEG (FIG. 3E).
Figure 3B:
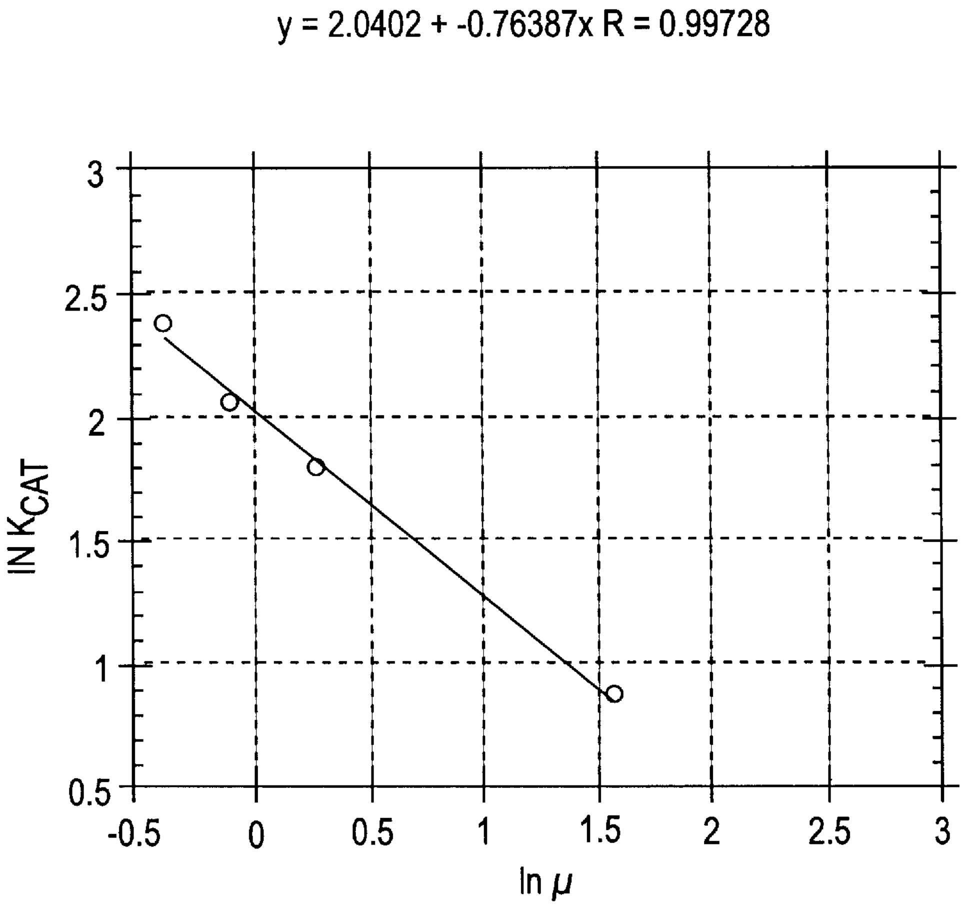
Figure 3C:
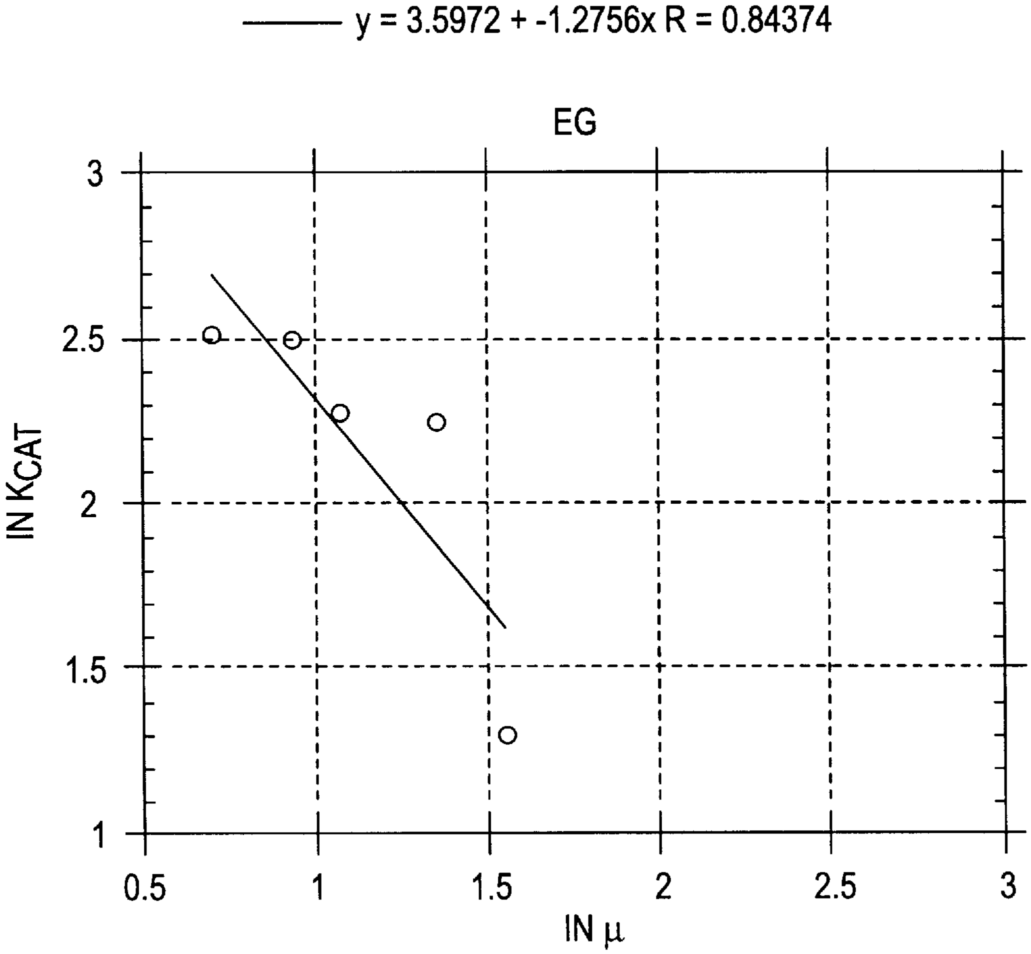
Figure 3D:
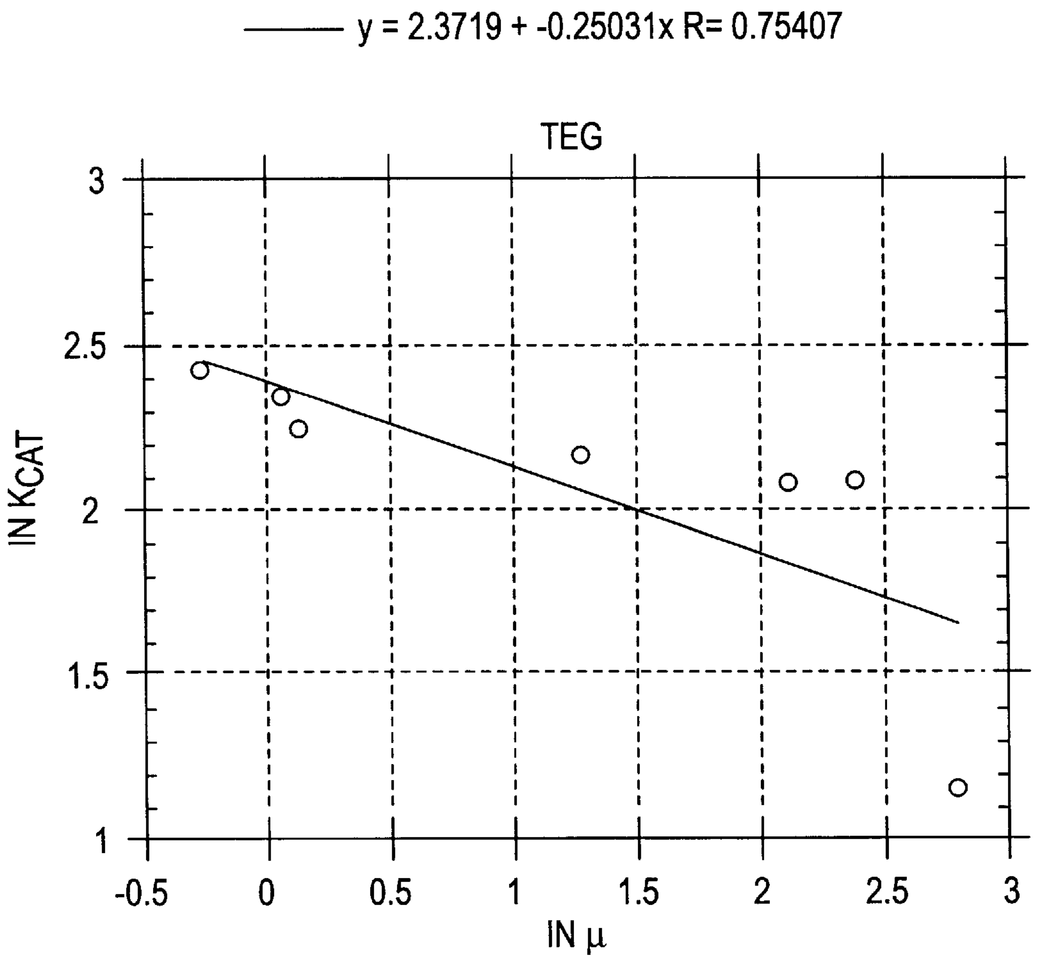
Figure 3E:
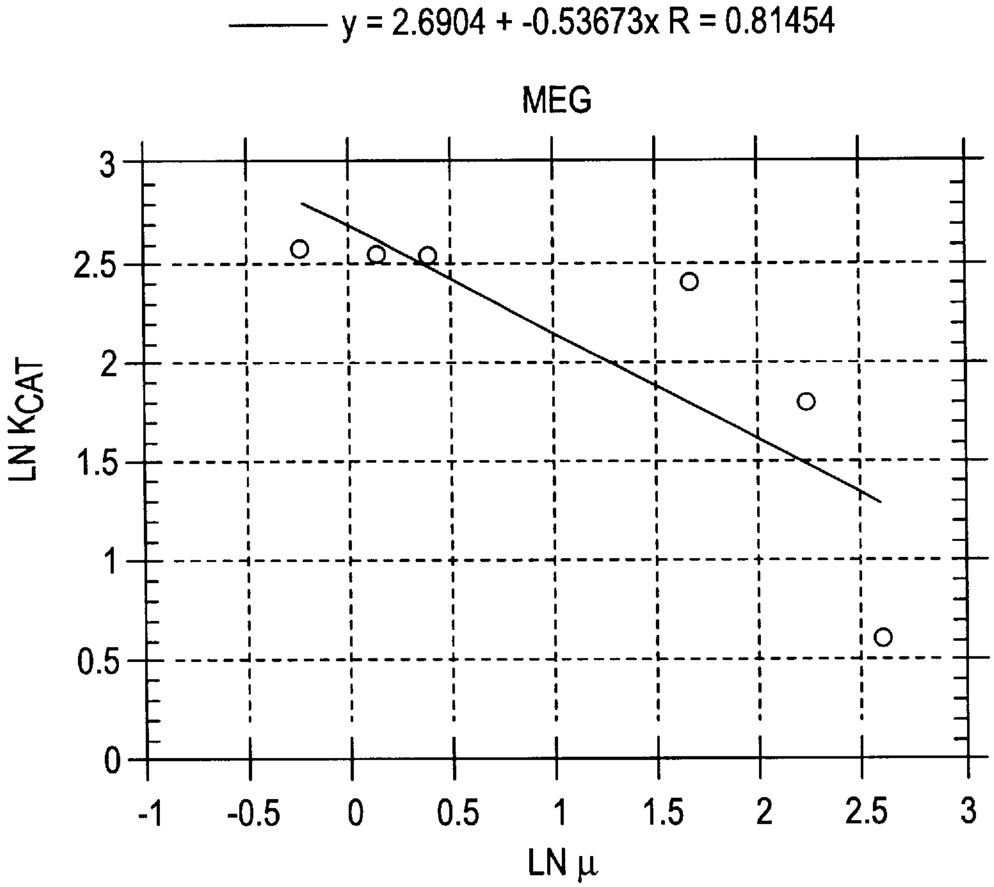

As shown in FIGS. 2A–2G, $k_{cat}$ increases at low cosolvent concentration, and decreases at higher concentrations, as the viscosity effect starts to dominate with EG (FIG. 2C) and MEG (FIG. 2F), and to a lesser extent with TEG (FIG. 2C) and PEG200 (FIG. 2E), but not with PEG8000 (FIG. 2G). With the longer EG-based cosolvents, the decrease in GA activity is less pronounced, and occurs at progressively higher viscosity values. No decrease was observed with PEG8000, although based on the trend observed, GA activity may decrease at very high viscosities not used in this study. The decrease in GA activity with solution viscosity is apparently rather complex, and is discussed in more detail in Example 3 below.

As discussed above, the effect of cosolvent viscosity on the turnover rate of GA toward maltose is shown in FIGS. 2A–2G for each of the seven cosolvents utilized. Five of the cosolvents, glycerol, PVP, EG, TEG and MEG, all substantially decreased $k_{cat}$ as the solution viscosity increased. A decrease in activity with increasing viscosity may be due to conformation limitations or to diffusional limitations. Diffusion of substrate into the active site of GA and initial substrate binding occur extremely rapidly as the entire process of substrate diffusion, binding and bond hydrolysis takes place over 4000-fold faster than the product release mechanism (Natarajan et al, *Biochem.*, 35:15269–15279 (1996)). Further, at the saturating substrate concentrations used for these studies, diffusional effects should not influence the reaction rate. The changes in the kinetic parameter, $k_{cat}$, caused by the increased solution viscosity therefore, can be attributed solely to changes in the rate-limiting product release step. The dependence of $k_{cat}$ on solution viscosity varies with each cosolvent. With PVP, GA activity started to decrease significantly at a viscosity around 1 cp, with glycerol, and with EG the decrease starts around 3.5 cp, with MEG around 6 cp, and with TEG around 15 cp. Only a slight decrease in activity is observed with PEG200 for solution viscosities up to 14 cp, and no decrease in activity was observed with PEG8000 for viscosities up to 18 cp. For the pure EG-based cosolvents, as the polymer length increases, the decrease in GA activity is not seen until progressively higher solution viscosities are obtained. This trend is not based on polymer length alone, since MEG decreased activity at lower viscosities than TEG, and PVP decreased activity at the lowest solution viscosity of any cosolvent. The change in the rate-limiting step due to solution viscosity is therefore, a function both of polymer length and polymer type.

Unlike the mixed effects observed on the decrease in activity of GA due to solution viscosity, a clear trend was observed in the increase in GA activity at low cosolvent concentrations. EG, the monomeric form of PEG, does not substantially start to increase $k_{cat}$ until a fairly high concentration, around 25% (w/v), is obtained, with a peak increase at around 50% (w/v). TEG, the tetrameric form, substantially increases activity at a lower concentration, around 5.0% (w/v), with a peak value around 10%. The TEG values are approximately 4-fold lower than the corresponding EG values, and corresponds to the fact that TEG has 4 EG units. PEG200 starts to significantly increase activity at a 1.0% (w/v) concentration, with a peak at 10% (w/v); MEG at 0.1% (w/v) concentration, with a peak at 10% (w/v), and PEG8000 at 0.01% (w/v), with a peak value at 1.0% (w/v). The longer the EG chain, the lower the concentration of cosolvent needed to facilitate the GA turnover rate. For any given concentration of cosolvent (% (w/v)), there are approximately the same number of total monomer units of EG present in each of the PEG related cosolvents (PEG200 and PEG8000 only have 1.4-fold more monomeric units than EG). The polymeric form of EG therefore, has a much more specific interaction with the enzyme than the monomeric form, and the longer the polymer, the more specific the interaction.

EXAMPLE 2

Effect of Temperature on Catalytic Rate

As shown in Example 1 above, the increase in GA activity by the cosolvents is due to a balance of two effects, the specific interaction with the enzyme and nonspecific viscosity effects. If the viscosity of the solution can be lowered without decreasing the specific interaction with the cosolvent, it should be possible to further increase the turnover rate of GA. While the mechanism of the specific interaction is not clear, the viscosity of a given cosolvent solution can be decreased by increasing the temperature. Since PEG8000 and MEG both produced substantial increases in the reaction rate, $k_{cat}$, at 45° C., the effect of these two cosolvents on the reaction rate was studied at a higher temperature, 60° C., to test whether viscosity could be decreased at higher temperature without also decreasing the specific interaction with the EG-based cosolvents. As shown in FIGS. 1F and 1G (and the above Table), both of these cosolvents resulted in a further 23% increase in activity at 60° C., giving a total increase in activity over the non-cosolvent reaction of around 65%. Since the shape of the curves shown in FIGS. 1F and 1G for both cosolvents are fairly similar at both 45° C. and 60° C., the increase in temperature does not substantially alter the $k_{cat}$ dependence on cosolvent concentration. At some of the low cosolvent concentrations used there should be negligible changes in the solution viscosity. At least in these, and possibly in all cases, the further increase in activity at 60° C. relative to the control with no cosolvent, cannot be attributed to a decrease in viscosity at the higher temperature, but must be attributed to some other effect. A likely explanation is that with the cosolvent present, a slightly different controlling mechanism is governing the rate-limiting step. This mechanism has a stronger temperature dependence than the non-cosolvent mechanism, accounting for a further increase in rate at higher temperatures.

EXAMPLE 3

Effect of Viscosity on Catalytic Rate

To further understand the interaction between the various cosolvents and the GA mechanism, additional analyses were carried out to elucidate the effect of viscosity on the GA mechanism.

As discussed above, if product release is the rate-limiting step in the GA mechanism, there should be a dependence of the $k_{cat}$ value on solution viscosity. If a conformational change associated with the product release is limiting the reaction rate, the relationship between $k_{cat}$ and viscosity, $\mu$, should be $\mu^{-\delta}$ (Demchenko et al, supra). This relationship is based on the Kramers' theory (Kramers, supra) which postulates that diffusional motion in a random field controls the rate at which the enzyme complex will pass over the activation energy barrier. However, if the rate-limiting step is not a unimolecular rearrangement, but, rather, the dissociation of product from the enzyme active site, the relationship between $k_{cat}$ and viscosity, $\mu$, should follow the relationship $e^{-\gamma\mu^2}$ (Somogyi et al, supra (1975); Somogyi et al, supra (1978); and Welch et al, supra). This relationship is based on the theory that the dissociating product must have a certain minimal kinetic energy to escape some characteristic volume in the enzyme active site. Once the product has exited from the characteristic volume, the product has a very low probability of reassociating. If the former relationship is valid, plots of $\ln(k_{cat})$ vs $\ln(\mu)$ for the various cosolvents should be linear with a slope of $-\delta$, whereas if the latter is true plots of $\ln(k_{cat})$ vs $(\mu)^2$ should be linear with a slope corresponding to $-\gamma$.

As shown in FIGS. 3A–3E, plots of $\ln(k_{cat})$ vs $\ln(\mu)$ were generally non-linear, except for the PVP plot. Neglecting the plots for PEG200 and PEG8000, which did not show substantial activity decreases with viscosity, the correlation coefficients were low, generally between 0.75 and 0.85, indicating a weak linear relationship.

Figure 4A:
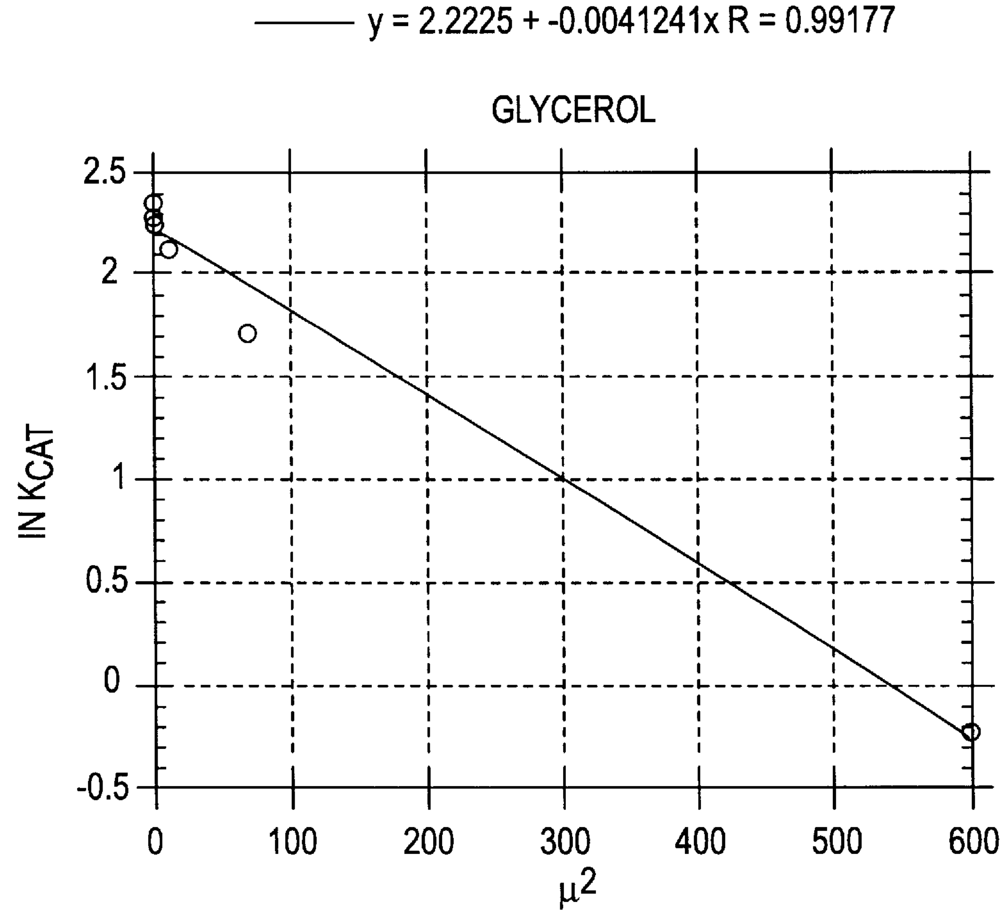
FIGS. 4A–4G show plots of $\ln(k_{cat})$ vs $(\mu)^2$ for maltose hydrolysis by GA at 45° C., 0.05M sodium acetate buffer (pH 4.5) in the presence of: glycerol (FIG. 4A); PVP (FIG. 4B); EG (FIG. 4C); TEG (FIG. 4D); PEG200 (FIG. 4E); MEG (FIG. 4F); and PEG8000 (FIG. 4G).
Figure 4B:
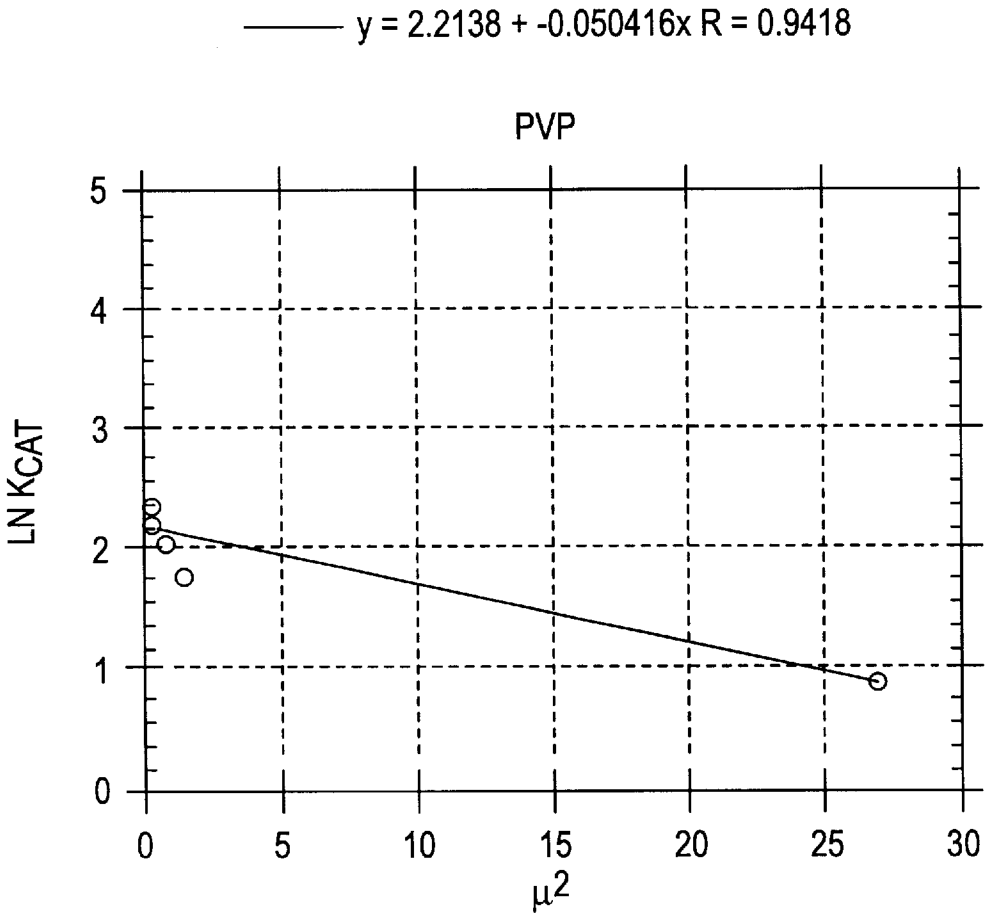
Figure 4C:
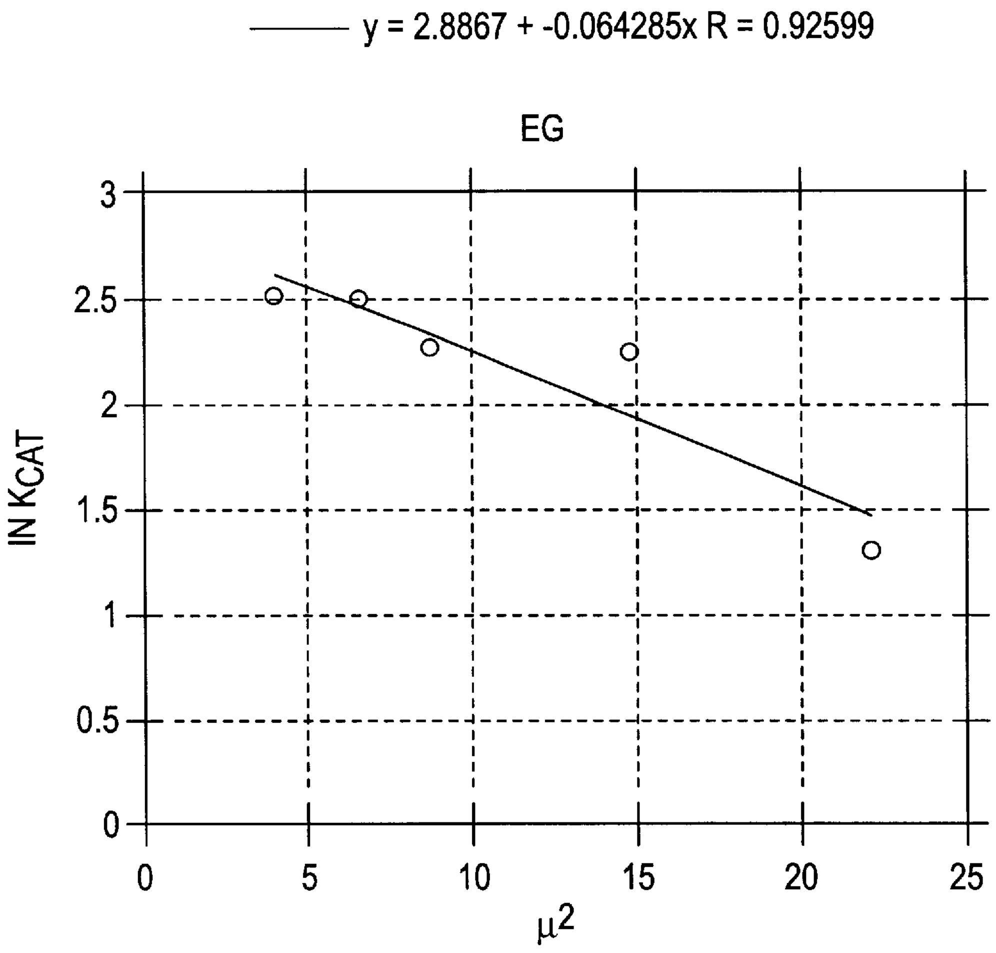
Figure 4D:
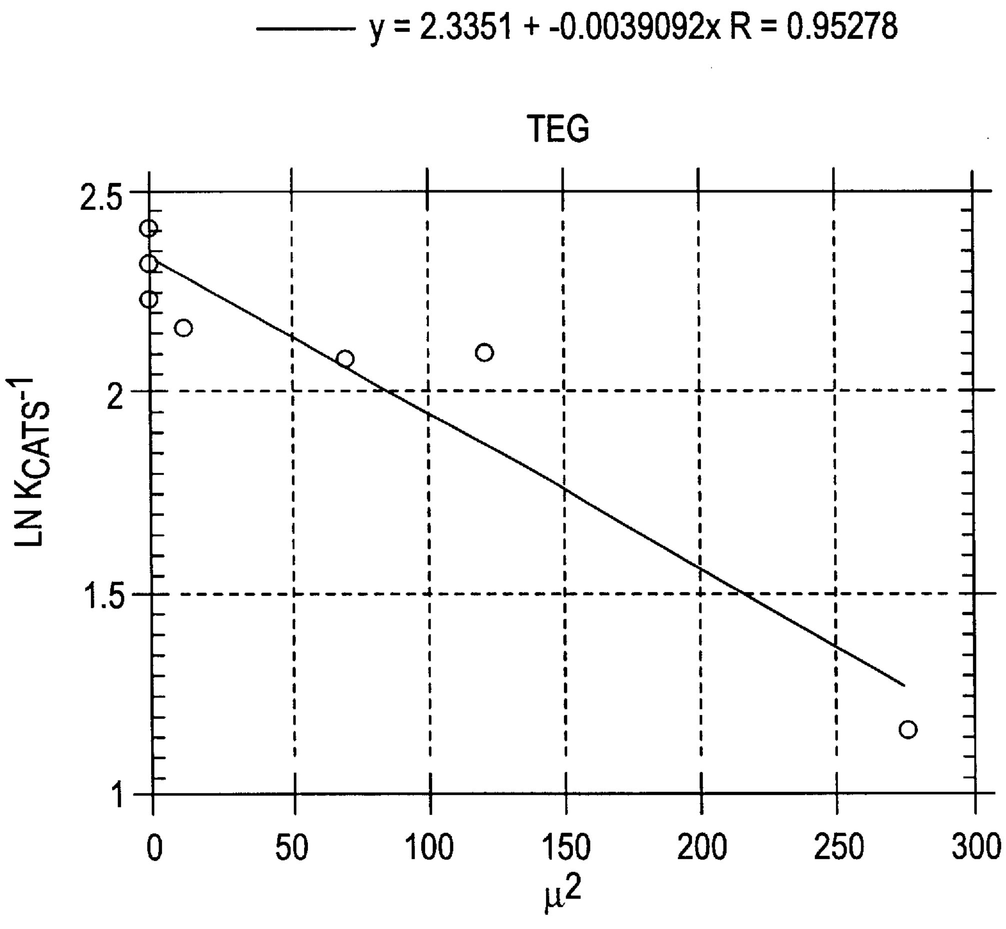
Figure 4E:
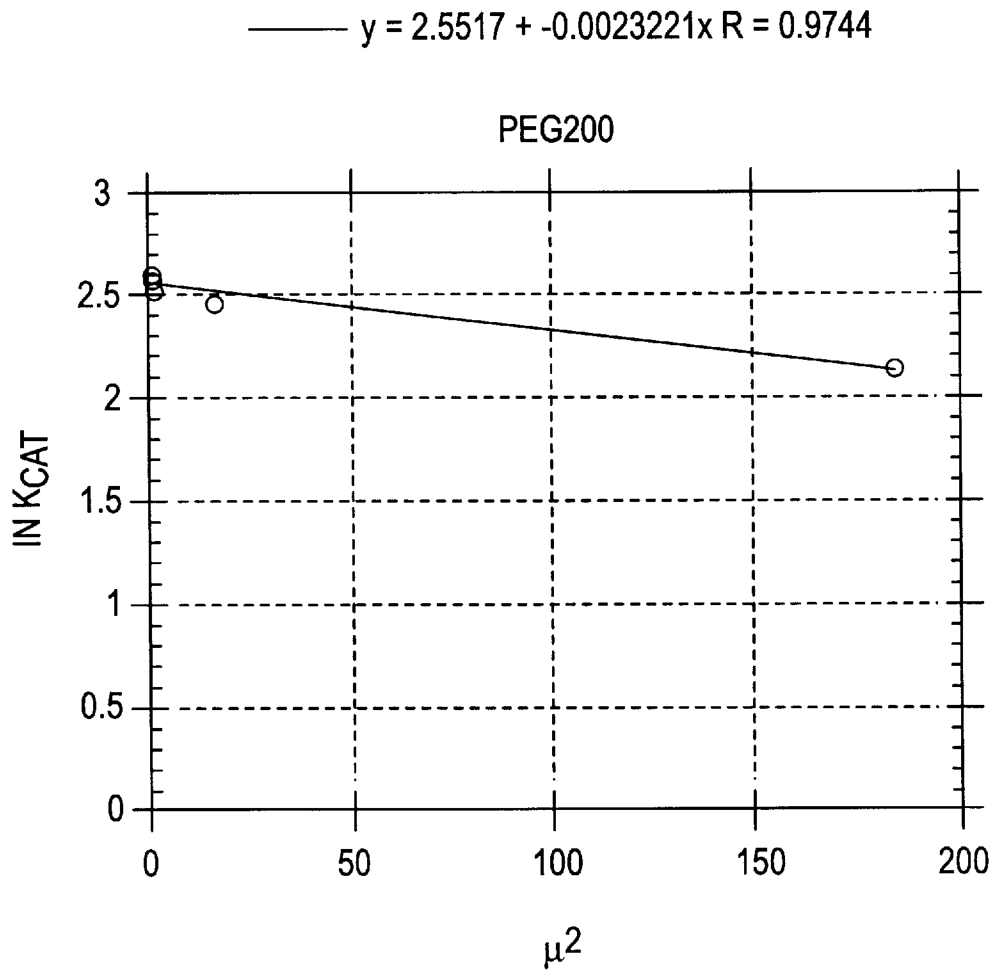
Figure 4F:
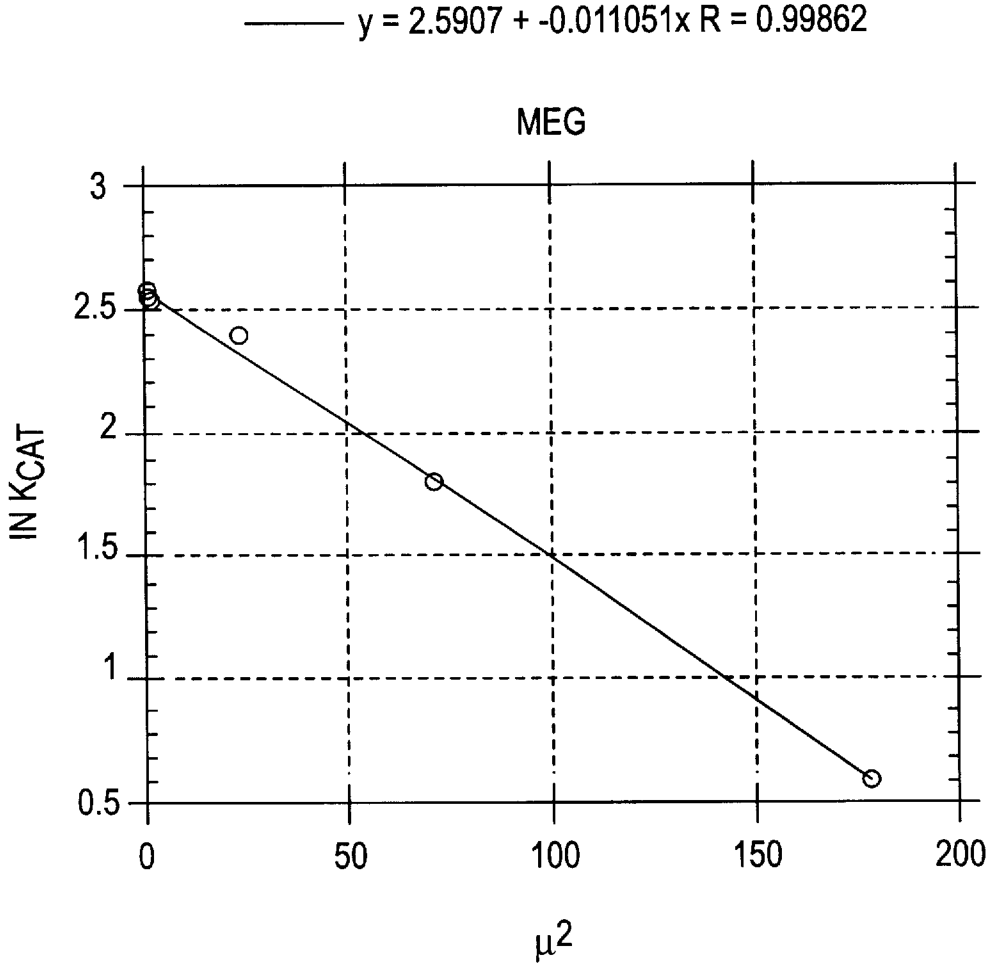
Figure 4G:
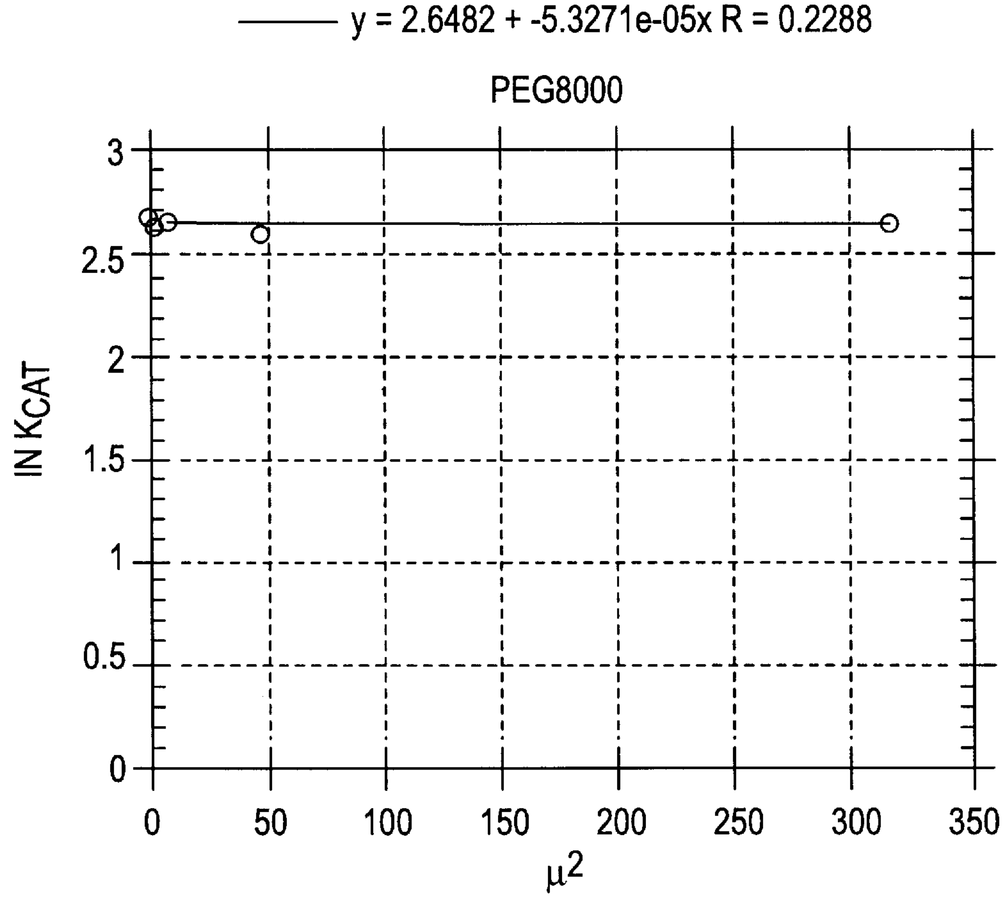

On the other hand, as shown in FIGS. 4A–4G, plots of $\ln(k_{cat})$ vs $(\mu)^2$ indicated a very good linear relationship. Again, neglecting again the PEG200 and PEG8000 plots, the correlation coefficients ranged from 0.93 to 1.00. Further, as shown in FIGS. 4A–4G, the plots of $\ln(k_{cat})$ vs $(\mu)^2$, while linear, have slightly varying slopes. The slope from these plots provide a value for $\gamma$, where $\gamma$ represents a function of various parameters, most of which should remain constant for a given enzyme and ligand system (Somogyi et al (1975), supra; and Somogyi et al (1978), supra). One parameter which may vary and change the value of $\gamma$ is the square of a distance factor representative of how far the product must travel to escape the active site "recognition volume". The slope may also change if a fraction of the energy normally transferred to the kinetic energy of the enzyme and product is redirected elsewhere (Welch et al, supra). The slopes from the plots in FIGS. 4A–4G range from −0.06 (with EG; FIG. 4C) to −0.004 (with TEG; FIG. 4D). This 15-fold difference in values for $\gamma$ may thus, be attributed to either a nearly 4-fold change in the "recognition volume", a substantial reduction in the kinetic energy transferred to the product, or a combination of the two effects.

When either PEG200 and PEG8000 were added to the reaction medium, the $k_{cat}$ value for maltose hydrolysis was essentially independent of solution viscosity. This independence of $k_{cat}$ on solution viscosity suggests that the rate-limiting step is no longer dependent on the product having the necessary energy to escape the enzyme active site. Either the active site in the presence of these polymers has very little affinity for the product essentially reducing the "recognition volume" to zero, and hence the value of the slope $\gamma$, or the Kinetic energy imparted to the product is much higher than seen when the other cosolvents are added or to a combination of these effects. The increase in activity starting at very low concentrations of these cosolvents, particularly of PEG8000, may be the result of an interaction between these polymers and the enzyme active site which fixes the active site in a conformation which releases product more efficiently.

When only the pure EG-based cosolvents are compared, it can be seen that the slopes obtained from the plots of $\ln(k_{cat})$ vs $(\mu)^2$ increase with polymer length. With these cosolvents there is a very consistent effect of cosolvent on the GA reaction mechanism. The longer the polymer, the more specific the interaction with the GA active site, as evidenced by the very low concentration of PEG8000 necessary to increase GA activity. Also, the longer the polymer, the less effect viscosity has on GA activity. These results suggest that the increase in activity seen at low concentrations is due to an interaction between the cosolvent and GA which makes it much easier for the product to escape the "recognition volume", either by imparting the maltose with significantly more energy or by decreasing the distance needed to escape the "recognition volume". The longer the EG-based cosolvent, the easier it is to escape the "recognition volume". MEG facilitates release of maltose from the "recognition volume", although the methyl substitution diminishes the effect at high viscosity. EG and PVP however do not alter the "recognition volume" significantly. Temperature affects this process as well, as with both PEG8000 and MEG an increase in temperature additionally facilitated escape from the "recognition volume".

These results described herein have important implications for the industrial application of GA in the food industry, particularly in the production of HFCS. Since GA is the rate-limiting step in this process, taking from 2–3 days, increasing the turnover rare of GA can decrease the process time significantly. PEG has also been approved for human consumption at varying concentrations depending on polymer size. The very low concentration of PEG8000 required to obtain over a 60% increase in the turnover rate of GA will not add substantially to the cost of the final product, and will significantly increase the production rate.

While the invention has been described in detail, and with reference to specific embodiments thereof, it will be apparent to one of ordinary skill in the art that various changes and modifications can be made therein without departing from the spirit and scope thereof.

What is claimed is:

1. A method for increasing the hydrolytic activity of a starch hydrolase comprising reacting a starch hydrolase with a substrate therefor in an aqueous reaction solution comprising a cosolvent of about 0.001 to 80% (w/v) of an ethylene glycol or polyethylene glycol, wherein said substrate is selected from the group consisting of maltose, isomaltose, maltodextrin and pullulan.

2. The method of claim 1, wherein said starch hydrolase is selected from the group consisting of glucoamylase, $\alpha$-amylase, $\beta$-amylase, amylo-1,6-$\alpha$-glucosidase, isomaltase, maltotriase, maltase, $\alpha$-glucosidase, cyclodextrinase, pullulanase, branching enzyme and glucanotransferase.

3. The method of claim 1, wherein said ethylene glycol or polyethylene glycol is in a concentration of from about 0.01 to 20% (w/v).

4. The method of claim 3, wherein said ethylene glycol or polyethylene glycol is in a concentration of from about 0.01 to 10% (w/v).

5. The method of claim 4, wherein said ethylene glycol or polyethylene glycol is present in an amount of from about 0.01 to 1.0% (w/v).

6. The method of claim 1, wherein said polyethylene glycol has a degree of polymerization of from 2 to 10,000.

7. The method of claim 6, wherein said polyethylene glycol has a degree of polymerization of from 200 to 8000.

8. The method of claim 1, wherein said polyethylene glycol is selected from the group consisting of tetraethylene glycol, polyethylene glycol 200, polyethylene glycol 8000, and methoxypolyethylene glycol.

9. The method of claim 1, wherein the temperature of the reaction is from 45° to 75° C.

10. The method of claim 9, wherein the temperature of the reaction is from 60° to 65° C.

* * * * *